(12) United States Patent
Thor et al.

(10) Patent No.: US 9,238,119 B2
(45) Date of Patent: Jan. 19, 2016

(54) INFUSION FLOW SYSTEM AND FLUID COUPLING

(75) Inventors: Eric J. Thor, Arden Hills, MN (US); Douglas J. Ball, Blaine, MN (US); Lief E. Leirfallom, Plymouth, MN (US); Michael J. Bonnette, Minneapolis, MN (US); Jason M. Bronstad, St. Francis, MN (US); Jason Anderson, Minnetonka, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 525 days.

(21) Appl. No.: 13/814,804

(22) PCT Filed: Aug. 11, 2011

(86) PCT No.: PCT/US2011/047409
§ 371 (c)(1),
(2), (4) Date: Feb. 7, 2013

(87) PCT Pub. No.: WO2012/021697
PCT Pub. Date: Feb. 16, 2012

(65) Prior Publication Data
US 2013/0138086 A1      May 30, 2013

Related U.S. Application Data

(60) Provisional application No. 61/373,080, filed on Aug. 12, 2010.

(51) Int. Cl.
*A61M 25/16* (2006.01)
*A61M 25/18* (2006.01)
(Continued)

(52) U.S. Cl.
CPC ........... *A61M 25/0014* (2013.01); *A61M 39/10* (2013.01); *A61M 39/1011* (2013.01);
(Continued)

(58) Field of Classification Search
CPC ..................... A61M 39/10; A61M 2039/1038; A61M 2039/1066; A61M 25/0014; A61M 39/1011; A61M 39/12; A61M 2025/0098
See application file for complete search history.

(56) References Cited

U.S. PATENT DOCUMENTS

| 1,436,707 A | 11/1922 | Gaschke |
| 2,564,804 A | 8/1951 | Everett |

(Continued)

FOREIGN PATENT DOCUMENTS

| EP | 313836 A2 | 3/1989 |
| EP | 254885 A1 | 2/1998 |

(Continued)

OTHER PUBLICATIONS

ANGIOJET Pump Set, Possis Medical, Inc. corporate website (www.possis.com).

(Continued)

*Primary Examiner* — Rebecca E Eisenberg
(74) *Attorney, Agent, or Firm* — Seager, Tufte & Wickhem, LLP

(57) ABSTRACT

Fluid infusion systems and fluid couplings are described herein. The infusion systems may include one or more fluid couplings used to make fluidic connection between a supply line and delivery tubing. The fluid couplings separate the functions of providing a seal around a delivery tube and retaining the delivery tube within the fluid coupling. The seal provided around the delivery tube prevents leakage around an exterior surface of a delivery tube such that fluid passing through the coupling must pass through the delivery tube rather than leak around the delivery tube. The structure used to retain the delivery tube in the fluid coupling prevents ejection of the delivery tube from the coupling due to the fluid pressures present in the coupling. The separate functions are performed by different structures within the fluid couplings.

20 Claims, 7 Drawing Sheets

(51) Int. Cl.
*A61M 25/00* (2006.01)
*A61M 39/10* (2006.01)
*A61M 39/12* (2006.01)

(52) U.S. Cl.
CPC ....... *A61M39/12* (2013.01); *A61M 2025/0098* (2013.01); *A61M 2039/1038* (2013.01); *A61M 2039/1066* (2013.01)

(56) References Cited

U.S. PATENT DOCUMENTS

| | | |
|---|---|---|
| 3,773,290 A | 11/1973 | Mowery |
| 4,039,266 A | 8/1977 | O'Connell |
| 4,122,556 A | 10/1978 | Poler |
| 4,166,807 A | 9/1979 | Komatsu et al. |
| 4,198,973 A | 4/1980 | Millet |
| 4,294,250 A | 10/1981 | Dennehey |
| 4,332,254 A | 6/1982 | Lundquist |
| 4,439,188 A | 3/1984 | Dennehey et al. |
| 4,447,077 A | 5/1984 | Palmer |
| 4,467,003 A | 8/1984 | Pallaroni et al. |
| 4,573,470 A | 3/1986 | Samson et al. |
| 4,573,966 A | 3/1986 | Weikl et al. |
| 4,636,195 A | 1/1987 | Wolinsky |
| 4,646,719 A | 3/1987 | Neuman et al. |
| 4,651,738 A | 3/1987 | Demer et al. |
| 4,653,539 A | 3/1987 | Bell |
| 4,710,075 A | 12/1987 | Davison |
| 4,710,171 A | 12/1987 | Rosenberg |
| 4,733,652 A | 3/1988 | Kantrowitz et al. |
| 4,758,223 A | 7/1988 | Rydell |
| 4,787,794 A | 11/1988 | Guthrie |
| 4,832,023 A | 5/1989 | Murphy Chutorian et al. |
| 4,838,268 A | 6/1989 | Keith et al. |
| 4,865,587 A | 9/1989 | Walling |
| 4,976,689 A | 12/1990 | Buchbinder et al. |
| 4,992,010 A | 2/1991 | Fischer |
| 5,014,494 A | 5/1991 | George |
| 5,045,061 A | 9/1991 | Seifert et al. |
| 5,059,176 A | 10/1991 | Winters |
| 5,059,178 A | 10/1991 | Ya |
| 5,066,286 A | 11/1991 | Ryan |
| 5,085,635 A | 2/1992 | Cragg |
| 5,106,363 A | 4/1992 | Nobuyoshi |
| 5,135,482 A | 8/1992 | Neracher |
| 5,147,164 A | 9/1992 | Fraver |
| 5,167,239 A | 12/1992 | Cohen et al. |
| 5,171,221 A | 12/1992 | Samson |
| 5,176,692 A | 1/1993 | Wilk et al. |
| 5,178,158 A | 1/1993 | de Toledo |
| 5,184,627 A | 2/1993 | de Toledo |
| 5,195,955 A | 3/1993 | Don Michael |
| 5,196,245 A | 3/1993 | DeRudder et al. |
| 5,207,656 A | 5/1993 | Kranys |
| 5,209,727 A | 5/1993 | Radisch, Jr. et al. |
| 5,209,740 A | 5/1993 | Bryant et al. |
| 5,211,636 A | 5/1993 | Mische |
| 5,217,438 A | 6/1993 | Davis et al. |
| 5,250,034 A | 10/1993 | Appling et al. |
| 5,320,604 A | 6/1994 | Walker et al. |
| 5,322,508 A | 6/1994 | Viera |
| 5,324,260 A | 6/1994 | O'Neill et al. |
| 5,328,472 A | 7/1994 | Steinke et al. |
| 5,330,450 A | 7/1994 | Lopez |
| 5,334,153 A | 8/1994 | McIntyre et al. |
| 5,368,034 A | 11/1994 | Isner |
| 5,378,236 A | 1/1995 | Seifert |
| 5,380,284 A | 1/1995 | Don Michael |
| 5,399,658 A | 3/1995 | Archey et al. |
| 5,410,797 A | 5/1995 | Steinke et al. |
| 5,413,581 A | 5/1995 | Goy |
| 5,474,194 A | 12/1995 | Heilman et al. |
| 5,476,450 A | 12/1995 | Ruggio |
| 5,505,699 A | 4/1996 | Forman et al. |
| 5,514,109 A | 5/1996 | Mollenauer et al. |
| 5,520,645 A | 5/1996 | Imran et al. |
| 5,549,556 A | 8/1996 | Ndondo Lay et al. |
| 5,549,557 A | 8/1996 | Steinke et al. |
| 5,554,114 A | 9/1996 | Wallace et al. |
| 5,583,047 A | 12/1996 | Blinka et al. |
| 5,584,843 A | 12/1996 | Wulfman et al. |
| 5,591,143 A | 1/1997 | Trombley, III et al. |
| 5,688,234 A | 11/1997 | Frisbie |
| 5,713,917 A | 2/1998 | Leonhardt et al. |
| 5,775,327 A | 7/1998 | Randolph et al. |
| 5,776,100 A | 7/1998 | Forman |
| 5,779,688 A | 7/1998 | Imran et al. |
| 5,779,721 A | 7/1998 | Nash |
| 5,792,179 A | 8/1998 | Sideris |
| 5,794,325 A | 8/1998 | Fallandy |
| 5,795,325 A | 8/1998 | Valley et al. |
| 5,807,330 A | 9/1998 | Teitelbaum |
| 5,810,871 A | 9/1998 | Tuckey et al. |
| 5,827,324 A | 10/1998 | Cassell et al. |
| 5,833,644 A | 11/1998 | Zadno Azizi et al. |
| 5,833,650 A | 11/1998 | Imran |
| 5,843,022 A | 12/1998 | Willard et al. |
| 5,865,721 A | 2/1999 | Andrews et al. |
| 5,879,361 A | 3/1999 | Nash |
| 5,881,534 A | 3/1999 | Ahlqvist et al. |
| 5,908,405 A | 6/1999 | Imran et al. |
| 5,925,016 A | 7/1999 | Chornenky et al. |
| 5,938,672 A | 8/1999 | Nash |
| 5,957,901 A | 9/1999 | Mottola et al. |
| 5,961,510 A | 10/1999 | Fugoso et al. |
| 5,968,017 A | 10/1999 | Lampropoulos et al. |
| 5,997,558 A | 12/1999 | Nash |
| 6,021,340 A | 2/2000 | Randolph et al. |
| 6,022,336 A | 2/2000 | Zadno Azizi et al. |
| 6,027,461 A | 2/2000 | Walker et al. |
| 6,036,715 A | 3/2000 | Yock |
| 6,050,972 A | 4/2000 | Zadno Azizi et al. |
| 6,071,285 A | 6/2000 | Lashinski et al. |
| 6,080,170 A | 6/2000 | Nash et al. |
| 6,123,698 A | 9/2000 | Spears et al. |
| 6,135,991 A | 10/2000 | Muni et al. |
| 6,146,372 A | 11/2000 | Leschinsky et al. |
| 6,161,695 A | 12/2000 | Nicolais |
| 6,166,116 A | 12/2000 | Sleeckx |
| 6,171,328 B1 | 1/2001 | Addis |
| 6,174,316 B1 | 1/2001 | Tuckey et al. |
| 6,176,844 B1 | 1/2001 | Lee |
| 6,179,816 B1 | 1/2001 | Mottola et al. |
| 6,183,420 B1 | 2/2001 | Douk et al. |
| 6,190,354 B1 | 2/2001 | Sell et al. |
| 6,203,561 B1 | 3/2001 | Ramee et al. |
| 6,217,567 B1 | 4/2001 | Zadno Azizi et al. |
| 6,224,570 B1 | 5/2001 | Le et al. |
| 6,231,588 B1 | 5/2001 | Zadno Azizi |
| 6,241,706 B1 | 6/2001 | Leschinsky et al. |
| 6,241,744 B1 | 6/2001 | Imran et al. |
| 6,245,008 B1 | 6/2001 | Leschinsky et al. |
| 6,245,089 B1 | 6/2001 | Daniel et al. |
| 6,251,093 B1 | 6/2001 | Valley et al. |
| 6,273,880 B1 | 8/2001 | Berg et al. |
| 6,355,016 B1 | 3/2002 | Bagaoisan et al. |
| 6,387,071 B1 | 5/2002 | Constantz |
| 6,475,185 B1 | 11/2002 | Rauker et al. |
| 6,485,657 B1 | 11/2002 | Funakoshi et al. |
| 6,488,671 B1 | 12/2002 | Constantz et al. |
| 6,494,314 B1 | 12/2002 | Lamborne et al. |
| 6,517,518 B2 | 2/2003 | Nash et al. |
| 6,524,323 B1 | 2/2003 | Nash et al. |
| 6,533,751 B2 | 3/2003 | Cragg et al. |
| 6,533,763 B1 | 3/2003 | Schneiter |
| 6,533,767 B2 | 3/2003 | Johansson et al. |
| 6,544,276 B1 | 4/2003 | Azizi |
| 6,569,147 B1 | 5/2003 | Evans et al. |
| 6,569,151 B1 | 5/2003 | Nash et al. |
| 6,612,990 B1 | 9/2003 | Pruter |
| 6,694,832 B1 | 2/2004 | Gleeson |
| 6,755,803 B1 | 6/2004 | Le et al. |
| 6,789,986 B2 | 9/2004 | Story, Jr. |
| 6,805,684 B2 | 10/2004 | Bonnette et al. |

(56) References Cited

U.S. PATENT DOCUMENTS

| | | |
|---|---|---|
| 6,824,550 B1 | 11/2004 | Noriega et al. |
| 6,830,577 B2 | 12/2004 | Nash et al. |
| 6,843,797 B2 | 1/2005 | Nash et al. |
| 6,855,136 B2 | 2/2005 | Dorros et al. |
| 6,869,417 B1 | 3/2005 | Walters et al. |
| 6,872,192 B2 | 3/2005 | Nash et al. |
| 6,875,193 B1 | 4/2005 | Bonnette et al. |
| 6,902,535 B2 | 6/2005 | Eberhart et al. |
| 6,905,505 B2 | 6/2005 | Nash et al. |
| 6,927,063 B2 | 8/2005 | Moreton et al. |
| 6,932,828 B2 | 8/2005 | Bonnette et al. |
| 6,936,056 B2 | 8/2005 | Nash et al. |
| 6,942,678 B2 | 9/2005 | Bonnette et al. |
| 6,962,707 B2 | 11/2005 | Schenk |
| 7,004,914 B2 | 2/2006 | Eberhart et al. |
| 7,048,696 B2 | 5/2006 | Eberhart et al. |
| 7,094,216 B2 | 8/2006 | Trombley, III et al. |
| 7,141,045 B2 | 11/2006 | Johansson et al. |
| 7,169,161 B2 | 1/2007 | Bonnette et al. |
| 7,219,799 B2 | 5/2007 | Bonnette et al. |
| 7,220,243 B2 | 5/2007 | Bonnette et al. |
| 7,226,425 B2 | 6/2007 | Eberhart et al. |
| 7,316,678 B2 | 1/2008 | Nash et al. |
| 7,334,681 B2 | 2/2008 | Bonnette et al. |
| 7,367,982 B2 | 5/2008 | Nash et al. |
| 7,374,560 B2 | 5/2008 | Ressemann et al. |
| 7,422,579 B2 | 9/2008 | Wahr et al. |
| 7,935,077 B2 | 5/2011 | Thor et al. |
| 8,162,878 B2 | 4/2012 | Bonnette et al. |
| 2001/0014821 A1 | 8/2001 | Juman et al. |
| 2001/0016704 A1 | 8/2001 | Zadno Azizi et al. |
| 2002/0096521 A1 | 7/2002 | Cardarelli |
| 2002/0133117 A1 | 9/2002 | Zadno Azizi et al. |
| 2003/0040705 A1 | 2/2003 | Dorros et al. |
| 2003/0208134 A1 | 11/2003 | Secrest et al. |
| 2004/0031721 A1 | 2/2004 | Mann |
| 2004/0039304 A1 | 2/2004 | Connors, III et al. |
| 2004/0039310 A1 | 2/2004 | Burkett |
| 2004/0050740 A1 | 3/2004 | Lewis |
| 2004/0059284 A1 | 3/2004 | Nash et al. |
| 2004/0097880 A1 | 5/2004 | Schur |
| 2004/0097995 A1 | 5/2004 | Nash et al. |
| 2004/0133185 A1 | 7/2004 | Nash et al. |
| 2004/0210164 A1 | 10/2004 | Eberhart et al. |
| 2005/0075647 A1 | 4/2005 | Walters et al. |
| 2005/0080357 A1 | 4/2005 | Eberhart et al. |
| 2005/0095891 A1* | 5/2005 | Schorn .............. A61M 39/1011 439/274 |
| 2005/0182437 A1 | 8/2005 | Bonnette et al. |
| 2005/0203425 A1 | 9/2005 | Langston |
| 2005/0271465 A1 | 12/2005 | Lehmann |
| 2006/0064123 A1 | 3/2006 | Bonnette et al. |
| 2006/0074318 A1 | 4/2006 | Ahmed et al. |
| 2006/0129126 A1 | 6/2006 | Kaplitt et al. |
| 2006/0282015 A1 | 12/2006 | Eberhart et al. |
| 2007/0060878 A1 | 3/2007 | Bonnette et al. |
| 2007/0060881 A1 | 3/2007 | Bonnette et al. |
| 2007/0073271 A1 | 3/2007 | Brucker et al. |
| 2007/0106245 A1 | 5/2007 | McQueen et al. |
| 2007/0118072 A1 | 5/2007 | Nash |
| 2007/0129679 A1 | 6/2007 | Bonnette et al. |
| 2008/0027334 A1 | 1/2008 | Langston |
| 2008/0097294 A1 | 4/2008 | Prather et al. |
| 2008/0100061 A1* | 5/2008 | Sage .................. A61B 5/6864 285/305 |
| 2008/0103456 A1 | 5/2008 | Johnson et al. |
| 2008/0188793 A1 | 8/2008 | Kozak et al. |
| 2008/0188831 A1 | 8/2008 | Bonnette et al. |
| 2008/0312671 A1 | 12/2008 | Riles et al. |

FOREIGN PATENT DOCUMENTS

| | | |
|---|---|---|
| WO | 02/24271 A2 | 3/2002 |
| WO | 02/009436 A2 | 11/2002 |
| WO | 2004018032 A1 | 3/2004 |
| WO | 2004/028592 A1 | 4/2004 |
| WO | 2006060688 | 10/2006 |
| WO | 2007053779 A2 | 5/2007 |
| WO | 2008157204 A3 | 12/2008 |

OTHER PUBLICATIONS

CRW (Radionics) Disposable Depth Stops Product No. DS11, DS16, DS18, DS21, DS25 and DS30, CRW Catalog Product Sheet, 2006.
MicroMewi Multiple Side hole Infusion Catheter Data Sheet, Micro Therapeutics, Inc., Feb. 2005.
ProStream Infusion Wire Data Sheet, EV3, Sep. 2007.
Supplementary European Search Report from related European Patent Application, mailed on Sep. 26, 2011.
Supplementary European Search Report issued Dec. 4, 2009 in corresponding European Application No. EP 05772444.5.
International Preliminary Report on Patentability of Related PCT Publication No. WO2008/157204 mailed on Dec. 9, 2008.
International Search Report and Written Opinion from corresponding PCT Application No. PCT/US11/47409 mailed on Dec. 11, 2011.
International Search Report for related International Application No. PCT/US2008/066646 mail on Dec. 9, 2008.
International Search Report of Related PCT Publication No. WO2008/157204, mailed on Dec. 17, 2009.

* cited by examiner

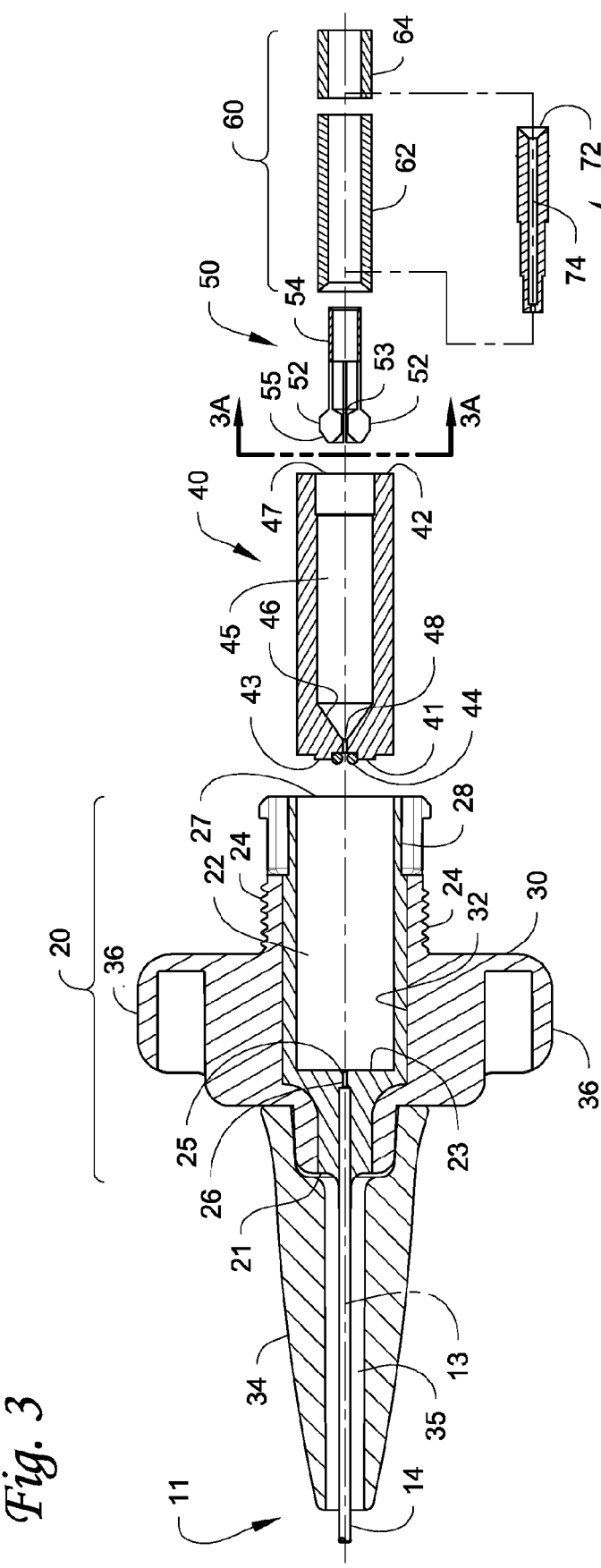

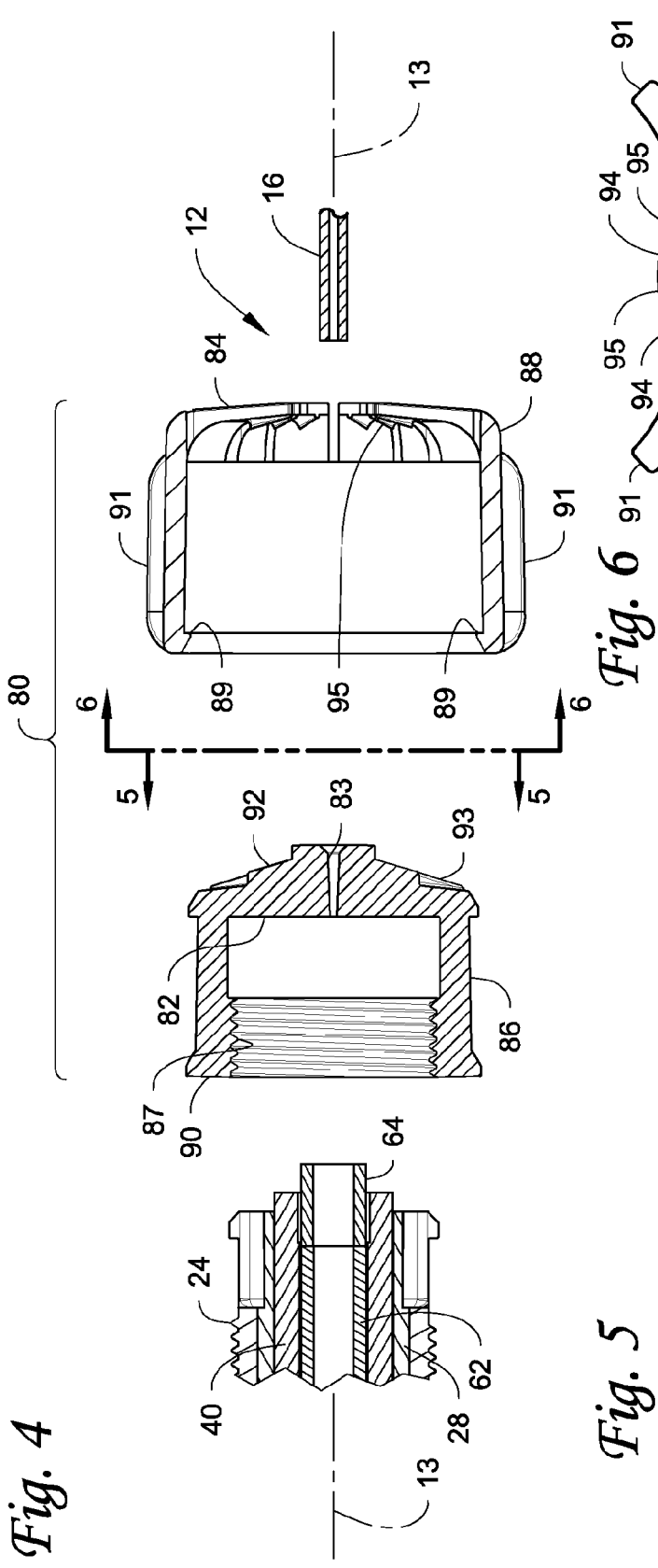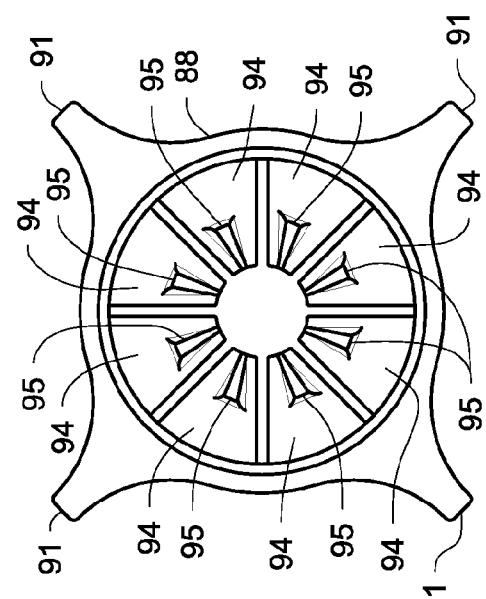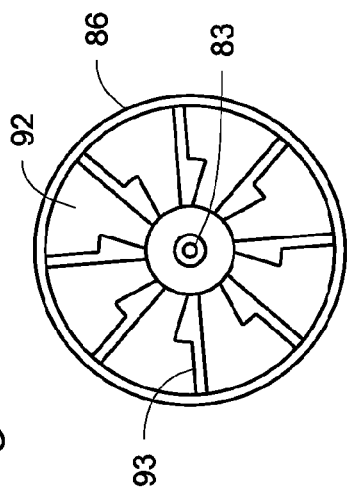

INFUSION FLOW SYSTEM AND FLUID COUPLING

CROSS REFERENCE TO RELATED APPLICATIONS

The present application is a 371 national phase application of PCT International Application No. PCT/US11/47409, filed on Aug. 11, 2011, and designating the United States of America, which claims the benefit under 35 U.S.C. §119(e) of U.S. Provisional Patent Application No. 61/373,080, filed on Aug. 12, 2010 which are hereby incorporated by reference in their entirety.

Infusion flow systems and fluid couplings used in the systems are described herein.

Catheters may use fluid pressure for a variety of different purposes. In some catheters, fluid may be delivered under pressure through one or more lumens to supply fluid jets that use the delivered fluid for a variety of purposes. One class of catheters that use fluid jets to deliver fluid under pressure are commonly referred to as thrombectomy catheters. Such catheters can be used to perform procedures in which thrombotic material is removed from a blood vessel (or other body lumen). The removed material may preferably be removed from the body through the thrombectomy catheter.

Another category of infusion flow systems that can be used with the fluid couplings described herein include infusion flow guidewires that infuse, for example, fibrinolytics. Such infusion flow guidewires are often very small with extremely small lumens and thus the ability to grip such wires without crimping or kinking is greatly enhanced by the fluid couplings disclosed herein.

Examples of some thrombectomy catheters or infusion flow guidewires are described in, e.g., U.S. Patent Application Publication US 2008/0188831 A1 (Bonnette et al.); U.S. Pat. No. 6,875,193 (Bonnette et al.); U.S. Pat. No. 6,805,684 (Bonnette et al.); U.S. Pat. No. 6,755,803 (Le et al.); U.S. Patent Application Publication US 2006/0064123 A1 (Bonnette et al.); U.S. Patent Application Publication No. US 2007/0129679 (Bonnette et al.); and U.S. Patent Application Publication No. US 2008/0312671 (Riles et al.).

SUMMARY

Infusion flow systems and fluid couplings are described herein. The systems may include one or more fluid couplings used to make fluidic connection between a supply line and delivery tubing.

The fluid couplings described herein preferably separate the functions of providing a seal around a delivery tube and retaining the delivery tube within the fluid coupling. The seal provided around the delivery tube preferably prevents leakage around an exterior surface of a delivery tube such that fluid passing through the coupling must pass through the delivery tube rather than leak around the delivery tube. The structure used to retain the delivery tube in the fluid coupling preferably prevents ejection of the delivery tube from the coupling due to the fluid pressures present in the coupling. The separate functions are performed by different structures within the fluid couplings in contrast to many conventional collet-based fluid couplings in which the same structures are used for both sealing and tube retention. It should, however, be understood that the structures used to perform the sealing and retention may also provide the other function, i.e., the seal structure may potentially assist at least partially with retention and, vice versa, the delivery tube retention structure may potentially at least partially seal around the exterior of the delivery tube. However, the sealing function could not effectively be performed by the retention structure, nor could the retention function be effectively performed by the sealing structure.

Although the systems described herein may use thrombectomy catheters, the thrombectomy catheters are described only for illustrative purposes. The infusion systems and fluid couplings described herein may be used with any catheter in which a fluidic connection between two different tubes or other fluid delivery lines is required. These systems may also be used with infusion flow guidewires as well, the delivery tube of which may be referred to as a flow wire.

In one aspect, some embodiments of the fluid coupling apparatus described herein may include a housing comprising a proximal end, a distal end, and a longitudinal axis extending between the proximal end and the distal end of the housing. The housing further comprises a primary bore comprising an opening facing the distal end of the housing and a proximal face located within the bore, the proximal face facing the distal end of the housing, and a supply line passage formed in the housing, the supply line passage extending from the proximal end of the housing to an opening in the proximal face of the primary bore. The fluid coupling further includes a sleeve comprising a proximal end located in the primary bore, wherein the sleeve further comprises a seal end facing the proximal face of the primary bore, a collet bore comprising a collet compression surface at a proximal end and an opening at a distal end, and a sleeve passage extending from the proximal end of the sleeve into the collet bore. The fluid coupling also includes a collet comprising a proximal end and distal end, wherein at least the proximal end of the collet is located in the collet bore of the sleeve, wherein the collet further comprises a plurality of collet fingers surrounding a collet passage, wherein each of the collet fingers comprises an inclined surface proximate the proximal end of the collet, wherein the inclined surfaces of the plurality of collet fingers are in contact with the collet compression surface of the sleeve such that movement of the collet in a proximal direction towards the proximal end of the housing forces the collet fingers towards a center of the collet passage. The fluid coupling also includes a compliance member comprising a proximal end in contact with the distal end of the collet, and wherein the compliance member comprises a resiliently compressible elastomeric polymer; and a collet compression member engaged with the housing, wherein the collet compression member comprises an inner surface, an outer surface facing away from the inner surface, and a tubing passage formed through the collet compression member from the inner surface to the outer surface. Advancement of the collet compression member in the proximal direction towards the proximal end of the housing causes the following: the inner surface of the collet compression member is forced against the distal end of the compliance member such that the proximal end of the compliance member is forced against the collet, the inclined surfaces of the plurality of collet fingers are forced against the collet compression surface of the sleeve, and the seal end of the sleeve is forced towards the proximal face of the primary bore.

In some embodiments of the fluid couplings described herein, a seal element is located between the proximal face of the primary bore and the seal end of the sleeve, and wherein advancement of the collet compression member in a proximal direction towards the proximal end of the housing compresses the seal element between the seal end of the sleeve and the proximal face of the primary bore. In some embodiments, the seal element comprises an O-ring attached to the seal end of the sleeve.

In some embodiments of the fluid couplings described herein the material forming the seal end of the sleeve is softer than the material forming the proximal face of the primary bore. For example, in some embodiments the seal end of the sleeve may be formed of polymeric material and the proximal face of the primary bore is formed of metallic material.

In some embodiments of the fluid couplings described herein, a guide member may be located in the collet passage, wherein the guide member comprises a guide bore extending from a guide surface at a distal end of the guide member towards a proximal end of the guide member.

In some embodiments of the fluid couplings described herein, the primary bore, the supply line passage, the collet bore, the collet passage, and the tubing passage are aligned along the longitudinal axis.

In some embodiments of the fluid couplings described herein, a supply tube is fixedly attached within the supply bore of the housing, wherein the supply tube extends in the proximal direction away from the proximal end of the housing.

In some embodiments of the fluid couplings described herein, the sleeve is constructed of a sleeve polymer, and wherein the resiliently compressible elastomeric polymer of the compliance member has a durometer that is less than a durometer of the sleeve polymer.

In some embodiments of the fluid couplings described herein, a distance between the seal end of the sleeve and the proximal end of the collet is less than a length of the sleeve between the proximal end and the distal end of the sleeve, wherein the distance and the length are measured along the longitudinal axis.

In some embodiments of the fluid couplings described herein, the proximal end of the collet is closer to the proximal end of the sleeve than to the distal end of the sleeve.

In some embodiments of the fluid couplings described herein, the collet compression member and the housing are threadably engaged with each other such that rotation of one or both of the collet compression member and the housing moves the inner surface of the collet compression member towards the proximal end of the fluid coupling.

In some embodiments of the fluid couplings described herein, the compliance member comprises a proximal tube and a distal tube, wherein the proximal tube is located proximally from the distal tube. In some embodiments, the distal tube is constructed of a resiliently compressible elastomeric polymer.

In another aspect, some embodiments of the fluid coupling apparatus described herein include a housing comprising a proximal end, a distal end, and a longitudinal axis extending between the proximal end and the distal end of the housing, wherein the housing further comprises: a primary bore comprising an opening facing the distal end of the housing and a proximal face located within the primary bore, the proximal face facing the distal end of the housing, and a supply line passage formed in the housing, the supply line passage extending from the proximal end of the housing to an opening in the proximal face of the primary bore. The fluid coupling further includes a sleeve comprising a proximal end located in the primary bore, wherein the sleeve further comprises: a seal cavity opening towards the proximal face of the primary bore, a collet bore comprising a collet compression surface at a distal end of the sleeve, wherein the collet bore opens towards the distal end of the sleeve, and a sleeve passage extending between the seal cavity and the collet bore. The fluid coupling further includes a retention mechanism retaining the sleeve in the primary bore and an amplifier piston located in the primary bore between the proximal face of the primary bore and the sleeve, wherein the amplifier piston comprises: a seal tip proximate a distal end of the amplifier piston, wherein the seal tip comprises a seal surface at the distal end of the amplifier piston, and wherein at least the seal surface of the seal tip is located in the seal cavity of the sleeve, a high pressure face at a proximal end of the amplifier piston, wherein the high pressure face faces the proximal surface of the primary bore, wherein the high pressure face comprises a larger surface area than the seal surface of the seal tip; a piston passage extending between the high pressure face and the seal surface of the amplifier piston. A piston seal is located between the proximal end and the distal end of the amplifier piston, wherein fluid from the opening in the proximal face of the primary bore is restricted from flowing between an exterior surface of the amplifier piston and an interior surface of the primary bore to the distal end of the amplifier piston. The fluid coupling further includes a seal element located in the seal cavity of the sleeve between the seal surface of the amplifier piston and a terminal surface of the seal cavity, wherein the seal element comprises a seal element passage extending through the seal element from a proximal end of the seal element to a distal end of the seal element, wherein the seal element comprises a resiliently compressible elastomeric polymer, and further wherein delivery of high pressure fluid through the fluid coupling apparatus forces the piston distally such that the seal element is compressed between the seal surface and the terminal surface of the seal cavity. A collet is also included in the fluid coupling, the collet comprising a proximal end located in the collet bore of the sleeve, wherein the collet further comprises: a plurality of collet fingers surrounding a collet passage, wherein each of the collet fingers comprises an inclined surface proximate the proximal end of the collet, wherein the inclined surfaces of the plurality of collet fingers are in contact with the collet compression surface of the sleeve such that movement of the collet in a proximal direction towards the proximal end of the housing forces the collet fingers towards a center of the collet passage. The fluid coupling further includes a collet compression member engaged with the sleeve, wherein the collet compression member comprises an inner surface, an outer surface facing away from the inner surface, and a tubing passage formed through the collet compression member from the inner surface to the outer surface, wherein advancement of the collet compression member in the proximal direction towards the proximal end of the housing forces the inclined surfaces of the plurality of collet fingers against the collet compression surface.

In some embodiments of the fluid couplings described herein, a biasing element is located in the primary bore, the biasing element forcing the piston proximally away from the sleeve.

In some embodiments of the fluid couplings described herein, the retention mechanism retaining the sleeve in the primary bore of the housing comprises a first snap-fit feature formed in an interior surface of the primary bore and a second snap fit feature formed in an outer surface of the sleeve, wherein the first snap fit feature and the second snap fit feature prevent removal of the sleeve from the primary bore in the absence of distortion of the sleeve and/or the housing.

In some embodiments of the fluid couplings described herein, the piston seal comprises an O-ring positioned around the exterior surface of the piston.

In some embodiments of the fluid couplings described herein, the primary bore, the seal cavity, the collet bore, and the collet passage are aligned along the longitudinal axis.

In some embodiments of the fluid couplings described herein, a supply tube is fixedly attached within the supply bore of the housing, wherein the supply tube extends in the proximal direction away from the proximal end of the housing.

In some embodiments of the fluid couplings described herein, the collet compression member and the housing are threadably engaged with each other such that rotation of one or both of the collet compression member and the housing moves the inner surface of the collet compression member towards the proximal end of the fluid coupling.

In some embodiments of the fluid couplings and the infusion flow systems described herein, the collet compression member comprises an inner nut and an outer sleeve fitted over the inner nut, wherein the inner surface of the collet compression member is located on the inner nut. In some embodiments, the inner nut and the outer sleeve comprise a plurality of ridges facing each other, wherein rotation of the outer sleeve about the longitudinal axis forces the ridges to interact to rotate the inner nut. In some embodiments, the ridges comprise a torque limiting structure such that the torque applied to the inner nut by the outer sleeve is limited when the ridges on the inner sleeve slip over the ridges on the inner nut when the outer sleeve is rotated in a first direction. In some embodiments, rotation of the outer sleeve about the longitudinal axis in a second direction that is opposite from the first direction results in absolute engagement between the ridges on the outer sleeve and the ridges on the inner nut.

In another aspect, some embodiments of an infusion flow system as described herein may include fluid supply apparatus; supply tubing comprising a proximal end connected to the fluid supply apparatus, wherein the supply tubing terminates at a distal end; and delivery tubing comprising a proximal end in fluid communication with the distal end of the supply tubing through a fluid coupling attached to the distal end of the supply tubing and the proximal end of the delivery tubing. The fluid coupling used in the infusion flow systems may be any of the fluid couplings described herein.

In some embodiments of the infusion flow systems described herein, the fluid coupling is capable of delivering fluid from the supply tubing to the delivery tubing when the fluid supply apparatus delivers fluid into the supply tubing at pressures of 10,000 psi or higher. In some embodiments, the delivery tubing comprises an outer diameter of 1 millimeter or less. In some embodiments, the delivery tubing comprises an outer diameter of 0.5 millimeter or less.

In some embodiments of the infusion flow systems described herein, the fluid coupling is capable of delivering fluid from the supply tubing to the delivery tubing when the fluid supply apparatus delivers fluid into the supply tubing at pressures of 15,000 psi or higher. In some embodiments, the delivery tubing comprises an outer diameter of 1 millimeter or less. In some embodiments, the delivery tubing comprises an outer diameter of 0.5 millimeter or less.

The words "preferred" and "preferably" refer to embodiments of the catheters and methods described herein that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, a fluid coupling may refer to one fluid coupling or more than one fluid coupling unless explicitly limited to, e.g., "only one fluid coupling."

The term "and/or" means one or all of the listed elements or a combination of any two or more of the listed elements.

The above summary is not intended to describe each embodiment or every implementation of the present concept. Rather, a more complete understanding of the concepts described herein will become apparent and appreciated by reference to the following Description of Illustrative Embodiments and claims in view of the accompanying figures of the drawing.

BRIEF DESCRIPTIONS OF THE VIEWS OF THE DRAWING

FIG. 3 is an exploded cross-sectional view of some of the components in the fluid coupling of FIGS. 1 and 2.

FIG. 3A is an end view taken from the proximal end of the collet along line 3A-3A in FIG. 3.

FIG. 3B is an alternate view of FIG. 3A after compression of the collet fingers.

FIG. 4 is an exploded cross-sectional view of some of the components of the fluid coupling of FIGS. 1 and 2.

FIG. 5 is a view, taken along line 5-5 in FIG. 4, of the outer surface of the inner nut of the collet compression member.

FIG. 6 is a view, taken along line 6-6 in FIG. 4, of the inner surface of the outer sleeve of the collet compression member.

DESCRIPTION OF ILLUSTRATIVE EMBODIMENTS

Figure 1:
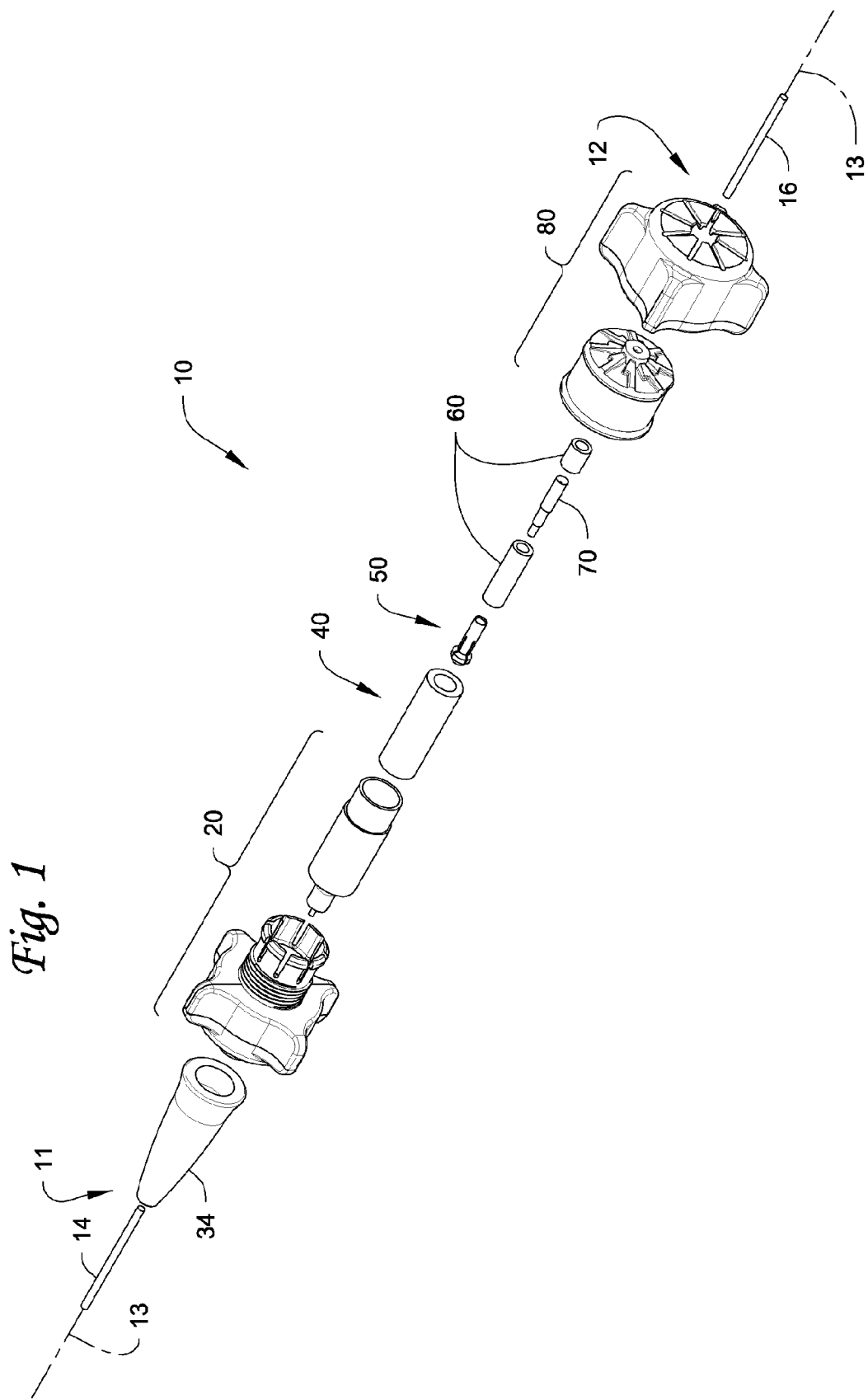
FIG. 1 is an exploded diagram of one exemplary fluid coupling that can be used in fluid delivery catheters as described herein.

In the following detailed description of illustrative embodiments, reference is made to the accompanying figures of the drawing which form a part hereof, and in which are shown, by way of illustration, specific embodiments of the catheters and methods. It is to be understood that other embodiments may be utilized and structural changes may be made without departing from the scope of the present disclosure.

Figure 2:
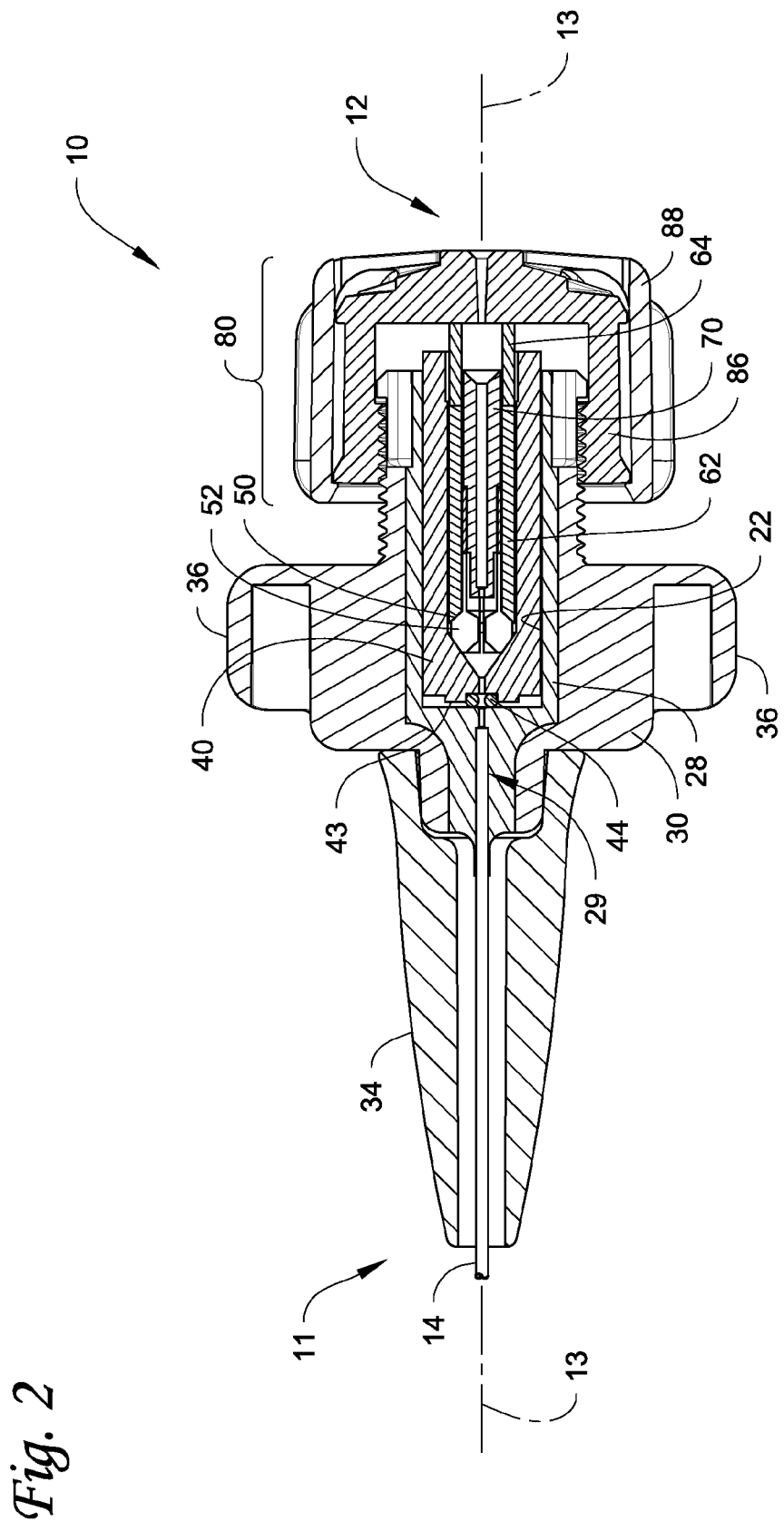
FIG. 2 is a cross-sectional view of the fluid coupling depicted in FIG. 1 (after assembly of the fluid coupling).

FIG. 1 is an exploded assembly diagram depicting the various component that may be provided in some embodiments of the fluid couplings as described herein, while FIG. 2 is an enlarged cross-sectional view of the fluid coupling 10 after the components have been assembled. FIG. 3 is an exploded cross-sectional view of some of the components in the fluid coupling of FIGS. 1 and 2 proceeding from the proximal end towards the distal end, while FIG. 4 is an exploded cross-sectional view of some of the components of the fluid coupling of FIGS. 1 and 2 proceeding from the distal end towards the proximal end. The coupling 10 is used to effect a fluid connection between a supply line 14 and a delivery tube 16.

The depicted embodiment of the fluid coupling 10 includes a proximal end 11 and a distal end 12, and the components of the fluid coupling 10 are assembled along a longitudinal axis 13. The various components in the fluid couplings as described herein may be described as having a proximal end and/or a distal end. As used herein, the proximal end of any such component is the end of the component that is nearest the proximal end 11 of the fluid coupling 10 and the distal end of any such component is the end of the component that is nearest the distal end 12 of the fluid coupling 10.

The fluid coupling 10 depicted in FIGS. 1-4 includes a housing 20, a sleeve 40 that fits within the housing 20, a collet 50 that fits within the sleeve 40, and a compliance member 60 that fits at least partially within the sleeve 40 on the distal end of the sleeve 40. The fluid coupling 10 also includes a compression member 80 and distal cap member 90 that retain the various components within the housing 20 from the distal end. The fluid coupling 10 of FIGS. 1-4 also includes an optional guide member 70 that fits within the sleeve 40.

The housing 20 of the fluid coupling 10 includes a primary bore 22 having an opening 27 that faces the distal end 12 of the fluid coupling 10. The primary bore 22 includes a proximal face 23 at its proximal end (i.e., the end of the primary bore 22 closest to the proximal end 11 of the fluid coupling 10).

The housing 20 also includes a supply line passage 26 formed therein, the supply line passage 26 extending from the proximal end 21 of the housing 20 to an opening 25 in the proximal face 23 of the primary bore 22 such that fluid passing through the supply line passage 26 in a distal direction (i.e., towards the distal end 12 of the fluid coupling 10) is delivered towards the primary bore 22 through the opening 25 in the proximal face 23.

The supply line passage 26 is preferably large enough such that a supply line 14 (as seen in FIG. 2) can be inserted into the supply line passage 26 to deliver fluid into the fluid coupling 10 from the proximal end 11 of the fluid coupling 10.

In the depicted embodiment, the housing 20 is provided in two subcomponents in the form of a housing insert 28 and a proximal cap 30. In such an embodiment, it may be preferred that a supply line 14 inserted into the supply line passage 26 (as depicted in FIG. 2) be fixedly attached to the housing insert 28. The attachment between the supply line 14 and the supply line passage 26 may be made by any suitable technique. If the supply line 14 and the housing insert 28 are constructed of metal (e.g., titanium, stainless steel, etc.), the supply line 14 may be attached to the housing insert 28 by a circumferential lap weld between the supply line 14 and the housing insert 28 (in zone 29 as depicted in FIG. 2).

The housing insert 28 is located within a cavity 32 in the proximal cap 30. In some embodiments, the housing insert 28 may be fixedly attached to the proximal cap 30 such that rotation of the housing insert 28 within the cavity 32 is restricted, while in other embodiments, the housing insert 28 may be allowed to rotate about the longitudinal axis 13 within the cavity 32.

In addition, the depicted embodiment of fluid coupling 10 includes a strain relief collar 34 attached to the proximal end 21 of the housing 20, such that a supply line 14 attached to the housing 20 extends through a lumen 35 in the strain relief collar 34 before entering the supply line passage 26. The strain relief collar 34 provides support to the supply line 14 to restrict bending of the supply line 14 at the point where the supply line 14 enters the proximal end 11 of the fluid coupling 10. An additional strain relief, not shown, may also be utilized on the distal end for similar purposes with the delivery tube. The strain relief collar 34 can be manufactured of many different materials, although it may be preferred that the materials used for the strain relief be resiliently flexible. Examples of some potentially suitable materials include, but are not limited to, urethanes, silicones, ethylene propylene diene monomer (EPDM) rubber, thermoplastic polyester elastomers (e.g., HYTREL (available from DuPont)), thermoplastic elastomers (e.g., SANTOPRENE (available from Exxon Mobil Corporation)), etc.

The proximal cap 30 may preferably include external features such as, e.g., fins 36 or other structures that can assist in manual control over rotation of the housing 20 about the longitudinal axis 13. In some embodiments, the housing insert 28 may preferably be constructed of metal (e.g., stainless steel, brass, etc.) while the proximal cap 30 may preferably be constructed of polymeric materials (e.g., polyester, polycarbonate, etc.). Still further, the strain relief collar 34 may be fixedly attached to the proximal cap 30 by any suitable technique, e.g., adhesives, overmolding, welding (thermal, chemical, etc.), snap-fitting, friction fit, etc.

The housing 20 may also preferably include threads 24 that cooperate with threads 87 on the compression member 80 to compress the components located between and/or within the housing 20 and the compression member 80 as described herein. In some embodiments that include a proximal cap 30 that receives a housing insert 28 in a cavity 32 (such as the depicted embodiment), the threads 24 may be provided on the proximal cap 30 (as depicted) and/or on the housing insert 28.

The fluid coupling 10 also includes sleeve 40 and at least a proximal end of the sleeve 40 is located within the primary bore 22 of the housing 20. In the depicted embodiment, the distal end 42 of the sleeve 40 extends out of the primary bore 22, but such an arrangement is not required (i.e., the distal end 42 of the sleeve 40 may be located within the primary bore 22 of the housing 20 in some embodiments).

The sleeve 40 further includes a seal end 43 facing the proximal face 23 of the primary bore 22. In some embodiments, a seal element 44 may be provided and located between the proximal face 23 of the primary bore 22 and the seal end 43 of the sleeve 40. In some embodiments, advancement of the collet compression member 80 as described herein in the proximal direction towards the proximal end 11 of the fluid coupling 10 compresses the seal element 44 between the seal end 43 of the sleeve 40 and the proximal face 23 of the primary bore 22.

In the depicted embodiment, the seal element 44 is in the form of a compressible O-ring, although the seal element 44 may take a variety of other forms in other embodiments, e.g., a gasket, etc. Although the depicted O-ring has a circular cross-sectional shape, O-rings/gaskets with other cross-sectional shapes could be used, e.g., square, trapezoidal, lobed (e.g., a four-lobed quad seal), etc. Also, although the seal element 44 in the depicted embodiment is attached to the sleeve 40 (inset into the seal end 43), the seal element 44 could alternatively be attached to the proximal face 23 of the primary bore 22 in other embodiments and, in still other embodiments, the seal element 44 could be simply located between the proximal face 23 and the seal end 43 without being attached to either housing 20 or the sleeve 40.

In addition to the seal element 44, in some embodiments a seal may be formed between the proximal face 23 of the primary bore 22 and the seal end 43 of the sleeve 40. That seal may be formed by, e.g., compression of the seal end 43 of the sleeve 40 against the proximal face 23. In some embodiments, the seal end 43 may preferably be made of material that is softer than the material use for the proximal face 23 of the primary bore 22. Softness may be measured using, e.g., the Shore A hardness scale or any other suitable equivalent. The softer material used for the seal end 43 of the sleeve 40 may, in some embodiments, conform to the shape of the proximal face 23 of the primary bore 22 to form a seal outside of the seal element 44 such that the flow of fluid from a supply tube 14 between the exterior surface of the sleeve 40 and the primary bore 22 is prevented (or at least substantially restricted).

In some embodiments, the seal end 43 may be made of a polymeric material while the proximal face 23 is made of a metal, while in other embodiments, the seal end 43 may be made of a metal that is softer than the metal used for the proximal face 23 of the primary bore 22. For example, the seal end 43 (and perhaps all of) the sleeve 40 may be constructed of, e.g., a nylon or another polymer (e.g., acetal, polycarbonate, acrylic, rigid polyurethane, etc.) while the proximal face 23 of the primary bore 22 may be a metal, e.g., stainless steel, brass, etc.

The sleeve 40 also includes a collet bore 45 formed therein that includes a collet compression surface 46 at the proximal end of the collet bore 45 and an opening 47 sized to receive a collet 50 at the distal end of the collet bore 45.

The collet compression surface 46 located at the proximal end of the collet bore 45 may preferably have a shape that cooperates with the collet 50 to force the collet fingers against a tube passing through the collet 50 as described herein. In the depicted embodiment, the collet compression surface 46 has a conical shape, although other non-conical shapes with tapering surfaces may also be used for the collet compression surfaces described herein.

The sleeve 40 further includes, in the depicted embodiment, a sleeve passage 48 that extends from the proximal end 41 of the sleeve 40 into the collet bore 45. Fluid from, e.g., a supply line located in the supply line passage 26 can preferably pass into the collet bore 45 through the sleeve passage 48 (in the absence of any element blocking the fluid passage 48).

In some embodiments, it may be preferred that the sleeve passage 48 be sized to allow a delivery tube as described herein to be advanced through the sleeve passage 48 such that its proximal end is located proximal to the proximal end 41 of the sleeve 40 and the seal element 44. When so positioned, the seal element 44 can form a fluid seal around the exterior of the delivery tube to prevent (or at least substantially restrict) fluid leakage around the outside of the delivery tube. At higher pressures, it is preferred that the delivery tube 16 extend through seal element 44 such that the proximal end of delivery tube 16 is proximal to the seal element 44.

The embodiment of fluid coupling 10 as depicted in FIGS. 1-4 also includes a collet 50 having at least its proximal end located in the collet bore 45 of the sleeve 40. The collet 50 preferably includes two or more collet fingers 52 that surround a collet passage 53 that extends from the proximal end of the collet 50 to the distal end of the collet 50.

The collet fingers 52 surrounding the collet passage 53 preferably extend from a collet base 54 that may be located closer to the distal end of the collet 50 such that the collet fingers 52 are essentially cantilevered from the collet base 54. Each of the collet fingers 52 preferably includes an inclined surface 55 proximate the proximal end of the collet 50.

When the collet 50 is assembled in a fluid coupling 10 such that the inclined surfaces 55 of the collet fingers 52 are in contact with the collet compression surface 46 of the sleeve 40, movement of the collet 50 in the proximal direction towards the proximal end 11 of the coupling 10 forces the collet fingers 52 towards a center of the collet passage 53. If a delivery tube 16 is located within collet passage 53, then the fingers 52 are forced against the delivery tube 16 as described herein. The forces applied by the collet fingers 52 on the delivery tube retain the delivery tube in position in the fluid coupling 10 with the proximal end of the delivery tube being located proximal of the proximal end 41 of the sleeve 40 such that the seal element 44 can for a seal around the delivery tube.

The collet passage 53 of the collet 50 may optionally have a minimum collapsed cross-sectional area of at least about 0.05 square millimeter ($mm^2$) or more. In other words, unlike some conventional collets, the collets used in connection with the fluid couplings described herein may include collet fingers that do not collapse to close the collet passage 53 in the absence of an article (such as, e.g., a tube, etc.) located in the collet passage 53. FIG. 3A is an end view taken from the proximal end of the collet 50 (along line 3A-3A in FIG. 3) depicting the collet passage 53 with the fingers 52 before compression. FIG. 3B is the same view taken when the collet fingers 52 are compressed such that the fingers 52 are all in contact with each other. Such a collet 50 may be manufactured by, e.g., boring out a conventional collet to provide the collet passage 53.

Where the fluid coupling in which the collet 50 is located is to be used with round tubes passing through the collet passage 53, the collet passage 53 may have a minimum collapsed diameter equal to or less than the outer diameter of the delivery tube passing through the collet 50 such that an adequate clamping force may be applied to the tube by the collet fingers 52.

The fluid coupling 10 of FIGS. 1-4 also includes a compliance element 60. The proximal end of the compliance element 60 acts on the collet fingers 52 to force the collet 50 in the proximal direction. The compliance element 60 depicted in FIGS. 1-4 is in the form of two components, a proximal sleeve 62 and the distal sleeve 64. The proximal end of the proximal sleeve 62 is in contact with and acts on the collet fingers 52, while the distal sleeve 64 acts on the distal end of the proximal sleeve 62. It may be preferred that at least one of the proximal sleeve 62 and the distal sleeve 64 include resiliently compressible elastomeric polymer that can be elastically deformed as the collet compression member 80 is advanced in the proximal direction to force the collet 50 into the collet bore 45 of the sleeve 40 as described herein.

In one embodiment, the proximal sleeve 62 may be in the form of a tube constructed of a first polymer while the distal sleeve 64 is in the form of a tube constructed of a second polymer, where the second polymer is a resiliently compressible elastomeric polymer. In such an embodiment, the proximal sleeve 62 may be constructed of, e.g., a nylon or another polymer (e.g., acetal, polycarbonate, acrylic, rigid polyurethane, etc.), although harder materials such as, e.g., metals, ceramics, etc. could be used). The distal sleeve 64 is constructed of, e.g., urethane or another resiliently compressible elastomeric polymer (e.g., rubbers, thermoplastic polyurethanes (such as, e.g., PELLETHANE 2363 90A (available from Dow Chemical), etc.), fluoroelastomers (e.g., VITON (available from DuPont Performance Elastomers), etc.), copolymers of butadiene and acrylonitrile (e.g., Buna-N, etc.), etc.).

Although the compliance element 60 is in the form of two sub-components in the depicted embodiment, in other embodiments the compliance element 60 may be provided as a single component. In such an embodiment, it may be preferred that some or all of the compliance element 60 be constructed of a resiliently compressible elastomeric polymer.

The embodiment of the fluid coupling 10 depicted in FIGS. 1-4 also includes an optional guide member 70 that is sized to fit within the collet 50 in the collet bore 45 of the sleeve 40. The guide member 70 includes a distal end 72 having a conical surface leading to a guide bore 74 that extends from the distal end 72 to the proximal end of the guide member 70. The guide member 70 may assist in aligning or guiding a delivery tube 16 inserted into the distal end 12 of the fluid coupling 10 with the collet passage 53 such that the delivery tube 16 can be advanced in the proximal direction through the collet passage 53. The guide member 70 is optional because, in some embodiments, the guide member 70 may not be required to guide the delivery tube 16 (where, e.g., the collet 50 itself includes guide structures, etc.). If provided, the guide member 70 may be constructed of any suitable material, e.g., polymer, ceramic, glass, metal, etc.

One relationship that is depicted in the embodiment of the fluid coupling illustrated in FIGS. 1-4 is the arrangement of the seal formed by the seal element 44 relative to the collet passage 53 as defined by the collet fingers 52 of the collet 50. In some embodiments, such as that depicted in FIGS. 1-4, the seal formed by seal element 44 is located proximally from the collet passage 53 located between collet fingers 52.

In some embodiments, a delivery tube (see, e.g., delivery tube 16 in FIG. 1) is advanced proximally through the collet passage 53 formed by the collet fingers 52 and, further, through the sleeve passage 48 such that the proximal end of the delivery tube is located proximally of the seal element 44 (such that the seal element 44 can form a seal around the exterior surface of the delivery tube). The delivery tube is further advanced proximally such that the proximal end of the delivery tube is located within the distal end of the supply line passage 26. In some embodiments, the opening 25 of the supply line passage 26 may be slightly widened with respect to the remainder of the supply line passage 26 to facilitate entry of the proximal end of the delivery tube into the opening 25 of the supply line passage 26.

The fluid coupling 10 depicted in FIGS. 1-4 also includes a collet compression member 80 located on the distal end 12 of the fluid coupling 10. The collet compression member 80 includes an inner surface 82, an outer surface 84 and a tubing passage 83 formed through the collet compression member 80, from the inner surface 82 to the outer surface 84, such that a delivery tube 16 can pass through the collet compression member 80 into the fluid coupling 10.

The collet compression member 80 is preferably engaged with the housing 20 such that the housing 20 and the collet compression member 80 can be advanced towards each other to provide the compressive force necessary to force the inner surface 82 of the collet compression member 80 against the distal end of the compliance member 60 (in the depicted embodiment, against the distal end of the distal sleeve 64). The compressive force provided by engagement of the collet compression member 80 with the housing 20 also forces the proximal end of the compliance member 60 against the collet 50 (in the depicted embodiment, the proximal end of the proximal sleeve 62 is forced against the collet 50).

The compressive force provided by engagement of the collet compression member 80 with the housing 20 also forces the inclined surfaces of the collet fingers 52 against the collet compression surface 46 of the sleeve 40. The result is that the collet fingers 52 are forced inward towards the collet passage 53 such that the collet 50 clamps onto a tube (e.g., a delivery tube 16) located within the collet passage 53.

The compressive force provided by engagement of the collet compression member 80 with the housing 20 also forces the seal end 43 of the sleeve 40 towards the proximal face 23 of the primary bore 22 in the housing 20. That compressive force may assist in forming seals by compressing the seal element 44 and/or the seal end 43 of the sleeve against the proximal face 23 of the primary bore 22.

FIG. 4 depicts the collet compression member 80 and the distal ends of the sleeve 40 and compliance member 60 (with the collet 50 and optional guide member 70 removed for clarity). The collet compression member 80, in the depicted embodiment, includes an inner nut 86 and an outer sleeve 88. The inner nut 86 preferably includes threads 87 designed to engage threads 24 on the housing 20 to provide the compressive forces described herein as the collet compression member 80 is advanced in the proximal direction using the threads 87 and the threads 24 on the housing 20.

The outer sleeve 88 is fitted over the inner nut 86 and may be retained thereon by a lip 89 that fits over the proximal edge 90 of the inner nut 86. The outer sleeve 88 may further include ribs 91 or other features on the outer surface to facilitate manual rotation of the outer sleeve 88.

Referring to FIG. 5, the outer surface 92 of the inner nut 86 preferably includes one or more ridges 93 that preferably extend outward from the center of the inner nut 86 (where the center is typically defined by the tubing passage 83 of the collet compression member 80). Although the depicted ridges 93 are oriented radially from the center of the inner nut 86, they may not necessarily be radially-oriented in all embodiments.

Referring to FIG. 6, the inner surface of the outer sleeve 88 preferably includes one or more ridges 95 that are located on cantilevered springs 94 that preferably extend inwardly towards the center of the outer sleeve 88 (where the center is typically defined by the tubing passage 83 of the collet compression member 80). The springs 94 are described as cantilevered because they are connected to the outer sleeve 88 at their outside ends, with their inside ends (in the center of the sleeve 88) being otherwise unconnected to the outer sleeve 88. As a result, a force on the springs 94 can deflect the inside ends of the springs 94 while the outside ends remain essentially unmoved relative to the outer sleeve 88. Although the depicted ridges are oriented radially relative to the center of the outer sleeve 88, they may not necessarily be radially-oriented in all embodiments. Also, in the depicted embodiment, each spring 94 includes one ridge 95, although in other embodiments, one or more of the springs 94 may include two or more ridges 95.

The ridges 93 on the inner nut 86 and the ridges 95 on the outer sleeve 88 preferably interact with each other in a manner that limits the torque that can be applied to the inner nut 86 using the outer sleeve 88, yet allows for removal or loosening of the inner nut 86 in a manner similar to that found on a ratcheting fuel cap used in the automobile industry. The tightening process may, in some embodiments, provide one or both of tactile and audible feedback for a user as the ridges 93 and 95 interact with each other during the tightening process. The interaction between the ridges 93 and 95 on the inner nut 86 and the outer sleeve 88 are depicted in FIGS. 7A and 7B.

Figure 7A:
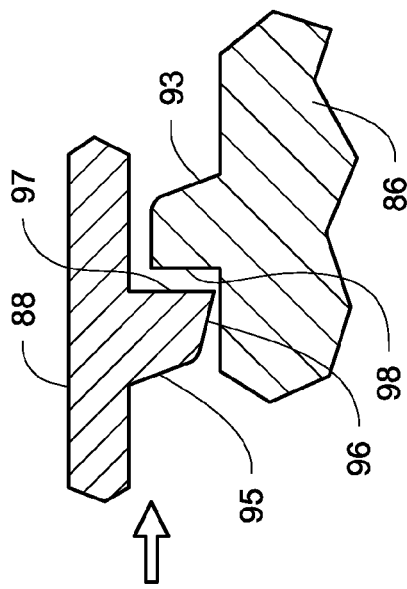
FIG. 7A is a schematic diagram depicting the relationship between the ridges when tightening the collet compression member on the housing, i.e., advancing the collet compression member in the proximal direction.

In FIG. 7A, the interaction between a ridge 93 on the inner nut 86 and a ridge 95 on the outer sleeve 88 during tightening of the collet compression member 80 is depicted in more detail. As seen in FIG. 7A, the ridge 95 may have an inclined surface 96. When a selected torque limit is exceeded as the outer sleeve 88 and the inner nut 86 are rotated about the longitudinal axis 13 (in the direction of the arrow in FIG. 7A) to provide the compressive force between the collet compression member 80 and the housing 20 as described herein, the ridge 95 having the inclined surface 96 rides up and over the ridge 93 on the inner nut 86.

Figure 7B:
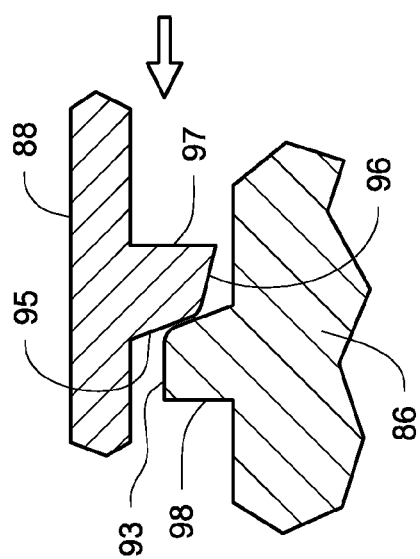
FIG. 7B is a schematic diagram depicting the relationship between the ridges when loosening the collet compression member on the housing, i.e., advancing the collet compression member in the distal direction.

In FIG. 7B, the interaction between the ridge 93 on the inner nut 86 and the ridge 95 on the outer sleeve 88 during loosening of the collet compression member 80 is depicted in more detail. As seen in FIG. 7B, the ridge 95 includes surface 97 and the ridge 93 includes surface 98 that act against each other during movement in the direction of the arrow depicted in FIG. 7B. Because the surfaces 97 and 98 interfere with each other and neither one is inclined, rotation of the outer sleeve 88 about the longitudinal axis 13 in the direction of the arrow in FIG. 7B, causes the inner nut 86 to rotate as well, thereby reducing the compressive force between the collet compression member 80 and the housing 20 as described herein.

In addition to the structures of the ridges 93 and 95, control over the torque (and, thus, the compressive force) that can be applied using the inner nut 86 and the outer sleeve 88 can be adjusted by changing the thickness, shape and other features of the springs 94 on which the ridges 95 are located because such changes can change the spring coefficient (and, thus, the force) applied by each spring 94. In addition to controlling the spring force provided by the springs, torque limit control can also be affected by changing the inclination angles of the inclined surfaces of the ridges, the interference between the ridges, etc.

In addition to structure, the materials used to construct the ridges 93 and 95, the springs 94, the inner nut 86, and the outer sleeve 88 may be selected to provide a desired torque limit while also maintaining the ability to loosen the inner nut 86 when desired. In some embodiments, for example, the inner nut 86 and the outer sleeve 88 may be constructed of, e.g., metals, polymers (e.g., polycarbonates, nylons, polyethylenes, acetals, etc.).

In some embodiments, the upper end of the torque limits provided by a collet compression member 80 as described herein may be on the order of, e.g., 1.4 Newton meters (about 12 in-lbs.) or less, in some embodiments 1.1 Newton meters (about 10 in-lbs.) or less. It may be preferred that the collet compression member 80 be capable of providing at least 0.7 Newton meters (about 6 in-lbs.) of torque.

Although the collet compression member 80 includes an inner nut 86 and an outer sleeve 88, in other embodiments, the collet compression member 80 may be provided in the form of a one-piece cap with threads and inner surface that is designed to work with the remainder of the fluid coupling as described herein. Such embodiments will not, however, typically provide the torque-limiting function of the two-piece collet compression member 80 as described herein.

The collet compression members used in the fluid couplings described herein may, in some embodiments, include features designed to retain the collet compression members on the fluid coupling even when the threads or other features used to provide the compressive force on the collet are not engaged. Examples of such features may include interfering shoulders on the inner surfaces of the inner nut 86 and the outer surface of the housing 20 that interfere with each other in a manner that restricts removal of the collet compression member from the fluid coupling when the collet compression member is not being used to compress the collet as described herein. In addition, restricting removal of the collet compression member from the fluid coupling even when they are not being used to compress the collet can be useful for retaining all of the components of the fluid coupling properly assembled.

The fluid couplings described herein may be provided in infusion flow systems, more specifically, the fluid couplings may be used in systems that include thrombectomy catheters or infusion flow guidewires as described in, e.g., U.S. Pat. No. 6,805,684 (Bonnette et al.); U.S. Pat. No. 6,875,193 (Bonnette et al.); U.S. Pat. No. 6,755,803 (Le et al.); U.S. Patent Application Publication US 2006/0064123 A1 (Bonnette et al.); U.S. Patent Application Publication No. US 2007/0129679 (Bonnette et al.); US Patent Application Publication US 2008/0188831 (Bonnette et al.); and U.S. Patent Application Publication No. US 2008/0312671 (Riles et al.).

Figure 8:
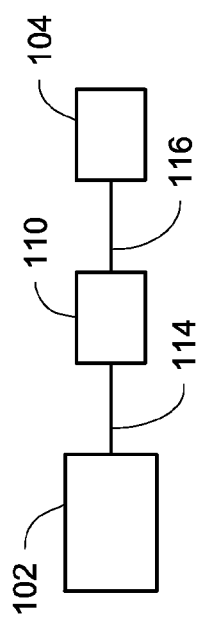
FIG. 8 depicts one illustrative embodiment of a system including a fluid coupling as described herein.

An illustrative embodiment of one system in which the fluid couplings described herein may be used is depicted schematically in FIG. 8, where a system 100 includes fluid supply apparatus 102 that is connected to a catheter 104 through a fluid coupling 110. The fluid supply apparatus 102, may include, e.g., a reservoir for containing a fluid to be delivered and a fluid pump capable of moving fluid from the reservoir to the fluid coupling 110 through the supply tubing 114 (See for example the systems disclosed in U.S. Pat. No. 7,935,077 (Thor et al.) or U.S. Pat. No. 7,094,216 (Trombley et al.) both of which are incorporated herein by reference). On the proximal or pump side of the fluid coupling 110, supply tubing 114 fluidly connects the fluid supply apparatus 102 to the fluid coupling 110. On the distal or catheter side of the fluid coupling 110, delivery tubing 116 carries fluid distally away from the fluid coupling 110 and the fluid supply apparatus 102 into and/or through the catheter 104.

The operating pressures of the fluid delivery systems in which the fluid couplings described herein may be used may, for example, range from 50 psi to 20,000 psi. The fluid delivery tubing 116 may, in some embodiments, be circular tubes with an outside diameter of about 0.014 inch (0.35 mm) and in inside diameter of about 0.010 inch (0.25 mm), although other tube profiles and/or dimensions may be used.

In some embodiments, the infusion flow systems described herein may include a fluid coupling 110 that is capable of delivering fluid from the supply tubing 114 to the delivery tubing 116 when the fluid supply apparatus 102 delivers fluid into the supply tubing 114 at pressures of 10,000 psi or higher. In other embodiments, the infusion flow systems described herein may include a fluid coupling 110 that is capable of delivering fluid from the supply tubing 114 to the delivery tubing 116 when the fluid supply apparatus 102 delivers fluid into the supply tubing 114 at pressures of 15,000 psi or higher. In some embodiments, the delivery tubing 116 may have an outer diameter of 1 millimeter or less, while in other embodiments, the delivery tubing 116 may have an outer diameter of 0.5 millimeter or less.

Figure 9:
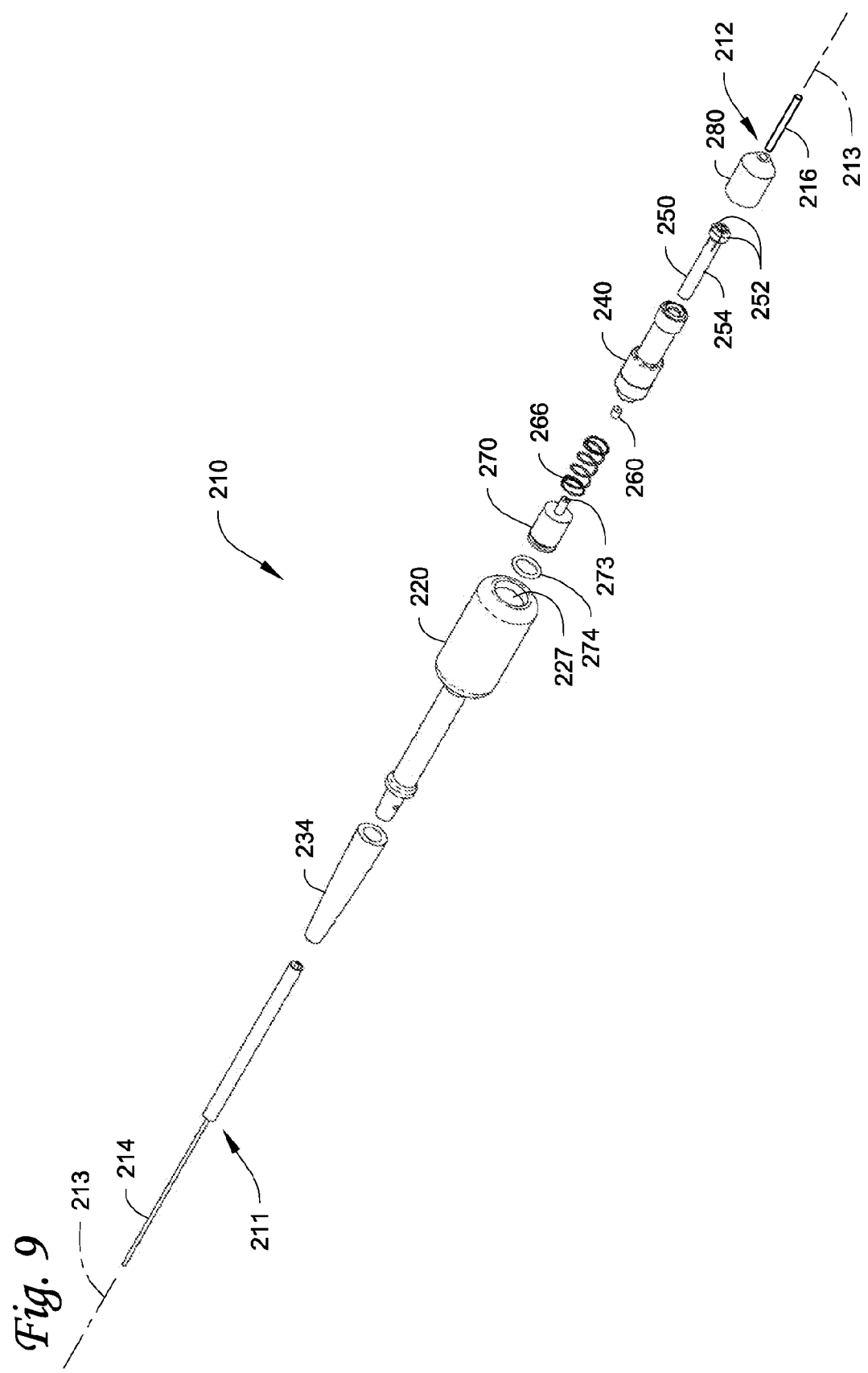
FIG. 9 is an exploded diagram of one alternative fluid coupling that can be used in fluid delivery catheters as described herein.
Figure 10:
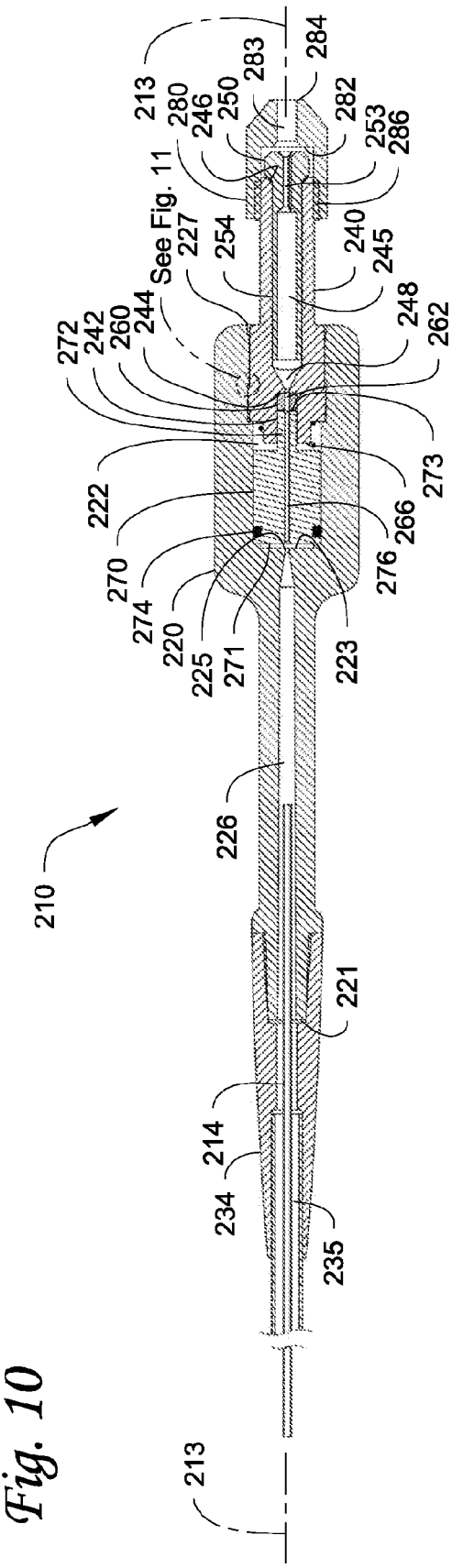
FIG. 10 is a cross-sectional view of the fluid coupling depicted in FIG. 9 (after assembly of the fluid coupling).

FIG. 9 is an exploded assembly diagram depicting the various component that may be provided in another illustrative embodiment of a fluid couplings as described herein (and which may be used in the system of FIG. 8), while FIG. 10 is an enlarged cross-sectional view of the fluid coupling 210 after the components have been assembled. The coupling 210 is used to effect a fluid connection between a supply line 214 and a delivery tube 216 (see, e.g., FIG. 9).

The alternative fluid coupling 210 depicted in FIGS. 9 and 10 includes a proximal end 211 and a distal end 212, and the components of the fluid coupling 210 are assembled along a longitudinal axis 213. As above, the various components in the fluid coupling 210 as described herein may be described as having a proximal end and/or a distal end. As used herein, the proximal end of any such component is the end of the component that is nearest the proximal end 211 of the fluid coupling 210 and the distal end of any such component is the end of the component that is nearest the distal end 212 of the fluid coupling 210.

The fluid coupling 210 depicted in FIGS. 9-10 includes a housing 220. A piston 270, seal element 260, and a sleeve 240 are arranged within the housing 220 as depicted. A collet 250 is fitted within the sleeve 240 and a collet compression member 280 retains the collet 250 within the sleeve 240.

The housing 220 of the fluid coupling 210 includes a primary bore 222 having an opening 227 that faces the distal end 212 of the fluid coupling 210. The primary bore 222 includes a proximal face 223 at its proximal end (i.e., the end of the primary bore 222 closest to the proximal end 211 of the fluid coupling 210).

The housing 220 also includes a supply line passage 226 formed therein, the supply line passage 226 extending from the proximal end 221 of the housing 220 to an opening 225 in the proximal face 223 of the primary bore 222 such that fluid passing through the supply line passage 226 in a distal direction (i.e., towards the distal end 212 of the fluid coupling 210) is delivered into the primary bore 222 through the opening 225 in the proximal face 223.

The supply line passage 226 is preferably large enough such that a supply line 214 can be inserted into the supply line passage 226 to deliver fluid into the fluid coupling 210 from the proximal end 211 of the fluid coupling 210.

In the depicted embodiment, the fluid coupling 210 includes a strain relief collar 234 attached to the proximal end 221 of the housing 220, such that a supply line attached to the housing 220 extends through a lumen 235 in the strain relief collar 234 before entering the supply line passage 226. The strain relief collar 234 preferably restricts kinking of the supply line 214 at the point where the supply line 214 enters the proximal end 211 of the fluid coupling 210. The strain relief collar 234 may be fixedly attached to the housing 220 by any suitable technique, e.g., adhesives, overmolding, welding (thermal, chemical, etc.). An additional strain relief, not shown, may also be utilized on the distal end for similar purposes with the delivery tube.

The housing 220 may, in some embodiments, include external features such as, e.g., fins or other structures that can assist in manual control over rotation of the housing 220 about the longitudinal axis 213.

The fluid coupling 220 includes a piston 270 located within the primary bore 222 of the housing 220. The piston 270 includes a high pressure face 271 at its proximal end 271, with the high pressure face 271 facing the proximal face 223 of the primary bore 222. The piston 270 also includes a seal tip 272 that includes a seal surface 273 at the distal end of the piston 270. The seal surface 273 faces the sleeve 240 and is located in a seal cavity 242 formed in the sleeve 240. In the depicted embodiment, the seal surface 273 acts on the seal element 260 located in the seal cavity 242 of the sleeve 240.

The high pressure face 271 of the piston 270 has a surface area facing the proximal direction that is greater than the surface area of the seal surface 273 that acts on the seal element 260. That difference in the relative surface areas may be useful in amplifying or concentrating the compressive force delivered to the seal element 260 by the seal surface 273 of the piston 270. In general the force delivered by the piston 270 is a function of the surface area of the high pressure face 271 and the fluid pressure of any fluid delivered to the primary bore 222 by a supply line threaded into the proximal end 211 of the coupling 210. That force is then largely transferred to the seal element 260 by the seal surface 273 of the piston 270.

The piston 270 also includes a piston passage 276 that extends through the piston from the high pressure face 271 at its proximal end to the seal surface 273 of the seal tip 272 at the distal end of the piston. The piston passage 276 provides a path through which fluid from the opening 225 in the proximal face 223 can flow through the piston 270 towards the distal end of the fluid coupling 210.

The fluid coupling 210 also includes a piston seal 274 located between the proximal end and the distal end of the piston 270. The piston seal 274 preferably functions to prevent fluid delivered into the primary bore 222 (through opening 225 in the proximal face 223) from flowing between an exterior surface of the piston 270 and an interior surface of the primary bore 222 to the distal end of the piston 270. The piston seal 274 may take many different forms (e.g., gaskets, etc.). Although the depicted piston seal 274 is in the form of an O-ring has a circular cross-sectional shape, O-rings/gaskets with other cross-sectional shapes could be used, e.g., square, trapezoidal, lobed (e.g., a four-lobed quad seal), etc. Regardless of its form, it may be preferred that the seal 274 allows for translational movement of the piston 270 within the primary bore 222 while still performing its sealing functions.

As indicated above, the fluid coupling 210 also includes sleeve 240 and at least a proximal end of the sleeve 240 is located within the primary bore 222 of the housing 220. In the depicted embodiment, the distal end of the sleeve 240 is located outside of the primary bore 222, but such an arrangement is not required (i.e., the distal end of the sleeve 240 may potentially be located within the primary bore 222 of the housing 220 in some embodiments).

The sleeve 240 further includes a seal cavity 242 facing the piston 270 and the proximal face 223 of the primary bore 222, with the piston 270 located between the sleeve 240 and the proximal face 223 of the primary bore 222. The seal cavity 242 opens towards the piston 270 and the proximal face 223 of the primary bore 222 and receives (at least partially) the seal tip 272 such that the seal surface 273 is located within the seal cavity 242.

A seal element 260 is located within the seal cavity 242 between the seal surface 273 of the piston 270 and a terminal surface 244 of the seal cavity 242 (where the terminal surface 244 of the seal cavity 242 is located at the distal end of the seal cavity 242). The seal element 260 includes a seal element passage 262 extending through the seal element 260 from its proximal end to its distal end such that, for example, a delivery tube (seen in FIG. 9, but not in FIG. 10) can extend through the seal element 260 from the distal end 213 of the fluid coupling 210.

The seal element 260 preferably includes resiliently compressible elastomeric polymer in its construction such that when the piston 270 is forced in the distal direction (by, e.g., high pressure fluid located between the proximal face 223 of the primary bore 222 and the high pressure face 271 of the piston 270), the seal element 260 is compressed within the seal cavity 242 between the seal surface 273 and the terminal surface 244 of the seal cavity 242. That compression preferably causes the seal element 260 to form a seal around an exterior surface of delivery tubing passing through the seal element passage 262.

An optional biasing element 266 may be provided in the primary bore 222 of the housing 220 of the fluid coupling 210. The biasing element 266 is located in the primary bore 222 such that it forces the piston 270 proximally away from the sleeve 240. The biasing element 266 may not be needed if the seal element 260 is resilient enough to move the piston 270 in the proximal direction towards the proximal face 223 of the primary bore 222 in the absence of high pressure fluid acting on the high pressure face 271 of the piston 270.

Figure 11:
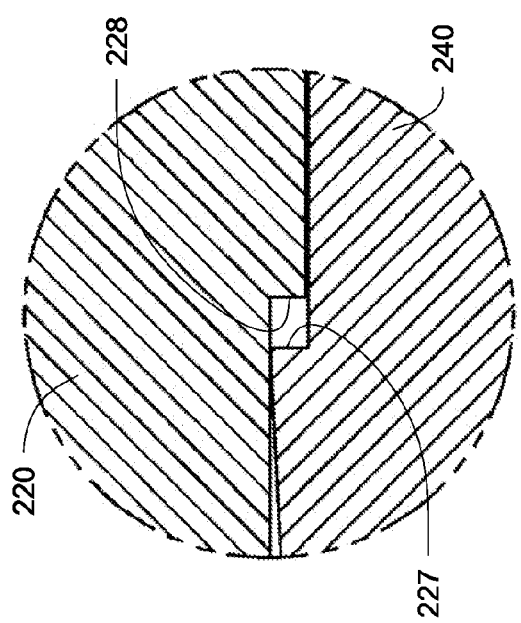
FIG. 11 is an enlarged cross-section view of the retention mechanism provided between the housing 220 and the sleeve 240 as seen in FIG. 10.

To provide the force on the piston 270, the sleeve 240 preferably resists movement in the distal direction, such that the sleeve 240 acts as a stop for the biasing element 266. The sleeve 240 can provide that stop function because the sleeve 240 is preferably retained within the primary bore 222 by a retention mechanism such that the sleeve 240, once inserted into the primary bore 222, cannot be removed without in some way releasing the retention mechanism. In the depicted embodiment and referring to FIG. 11 (which is an enlarged cross-section view of the retention mechanism provided in the embodiment depicted in FIGS. 9-10), the retention mechanism is provided in the form of a first snap-fit feature (e.g., lip 228) formed in the interior surface of the primary bore 222 and a second snap fit feature (e.g., lip 227) formed in the outer surface of the sleeve 240. The first lip 228 in the primary bore 222 and the second lip 227 on the sleeve 240 act against each other after insertion of the sleeve 240 into the primary bore 222 to prevent removal of the sleeve 240 from the primary bore 222 in the absence of distortion of the sleeve 240 and/or the housing 220.

Many other retention mechanisms could be substituted for the depicted mechanism provided the retention mechanisms are capable of retaining the sleeve 240 in the primary bore 222. Examples of some potentially useful alternative retention mechanisms may include, but are not limited to, a threaded or snap-fit collar positioned over the distal end of the housing 220, etc. In some embodiments, it may be possible to use adhesives, welding (thermal, chemical, etc.) in place of a mechanical retention mechanism to retain the sleeve 240 in the primary bore 222 of the housing 220.

The biasing element 266 as depicted in FIGS. 9-10 is in the form of a coil spring, although where a biasing element is provided, many other basing elements could be used in place of or in addition to a coil spring, e.g., resilient elastomeric plugs, etc.

In addition to the seal cavity 242, the sleeve 240 includes a collet bore 245 formed therein that includes a collet compression surface 246 at the proximal end of the collet bore 245 and an opening sized to receive a collet 250 at the distal end of the collet bore 245.

The sleeve 240 further includes, in the depicted embodiment, a fluid passage 248 that extends from the seal cavity 242 into the collet bore 245. Fluid from, e.g., a supply line located in the supply line passage 226, can preferably pass into the collet bore 245 through the fluid passage 248 (in the absence of any element blocking the fluid passage 248).

In some embodiments, it may be preferred that the fluid passage 248 be sized to allow a delivery tube as described herein to be advanced through the fluid passage 248 such that its proximal end is located proximal to the seal element 260. It is preferred at higher pressures that the proximal end of the delivery tube be advanced proximally through the fluid coupling 210 from the distal end 212 until the proximal end of the delivery tube is located within the supply line passage 226 of the housing 220.

The collet 250 preferably includes at least its proximal end located in the collet bore 245 of the sleeve 240. Collet 250 used in fluid coupling 210 is preferably similar to collet 50 described herein in connection with fluid coupling 10, i.e., collet 250 preferably includes two or more collet fingers 252 that surround a collet passage 253 that extends from the proximal end of the collet 250 to the distal end of the collet 250. It is preferred that fluids can pass into the collet passage from the collet bore 245 of the sleeve 240 when the collet 250 is located in the collet bore 245 of the sleeve 240.

The collet compression surface 246 located at the proximal end of the collet bore 245 may preferably have a shape cooperates with the collet 250 to force the collet fingers 252 against a delivery tube passing through the collet passage 253 as described herein. In the depicted embodiment, the collet compression surface 246 has a conical shape, although other non-conical shapes with tapering surfaces may also be used for the collet compression surfaces described herein.

The collet fingers 252 surrounding the collet passage 253 preferably extend from a collet base 254 that may be located closer to the distal end of the collet 250 such that the collet fingers 252 are essentially cantilevered from the collet base 254. Each of the collet fingers 52 preferably includes an inclined surface proximate the proximal end of the collet 250.

When the collet 250 is assembled in a fluid coupling 210 such that the inclined surfaces of the collet fingers 252 are in contact with the collet compression surface 246 of the sleeve 240, movement of the collet 250 in the proximal direction towards the proximal end 211 of the coupling 210 forces the collet fingers 252 towards a center of the collet passage 253. If a delivery tube is located within collet passage 253, then the fingers 252 are forced against the delivery tube as described herein to retain the delivery tube within the fluid coupling 210.

The collet passage 253 of the collet 250 may optionally have a minimum collapsed cross-sectional area of at least about 0.05 square millimeters ($mm^2$) or more. In other words, unlike some conventional collets, the collets used in connection with the fluid couplings described herein may include collet fingers that do not close the collet passage 253 when collapsed in the absence of an article (such as, e.g., a tube, etc.) located in the collet passage 253 (see, e.g. FIGS. 3 and 3A and the corresponding discussion in connection with collet 50). Where the fluid coupling in which the collet 250 is located is to be used with round tubes passing through the collet passage 253, the collet passage 253 may have a minimum collapsed diameter that is equal to or less than the outer diameter of the tube passing through the collet 250 such that an adequate clamping force may be applied to the tube by the collet fingers 252.

The fluid coupling 210 depicted in FIGS. 9-10 also includes a collet compression member 280 located on the distal end 212 of the fluid coupling 210. The collet compression member 280 includes an inner surface 282, an outer surface 284 and a tubing passage 283 formed through the collet compression member 280, from the inner surface 282 to the outer surface 284, such that a delivery tube can pass through the collet compression member 280 into the fluid coupling 210.

The collet compression member 280 is preferably engaged with the sleeve 240 such that the sleeve 240 and the collet compression member 280 can be advanced towards each other to provide the compressive force need to force the inner surface 282 of the collet compression member 280 against the distal end of the collet 250.

In some embodiments, the sleeve 240 and the collet compression member 280 may include complementary threads 286 such that rotation of the collet compression member 280 about the axis 213 moves the collet compression member 280 in the proximal direction. In some embodiments, the collet compression member 280 could extend to the housing 220 and connect their (by, e.g., threads, etc.) rather than the sleeve 240. Also, although threads 286 are used in the depicted embodiment, any other suitable connection could be used in place of threads, e.g., a ratcheting connection, snap fitting, etc.

The compressive force provided by engagement of the collet compression member 280 with the sleeve 240 also forces the inclined surfaces of the collet fingers 252 against the collet compression surface 246 of the sleeve 240. The result is that the collet fingers 252 are forced inward towards the collet passage 253 such that the collet 250 clamps onto a tube located within the collet passage 253.

Although not depicted in connection with the embodiment of FIGS. 9-10, the collet compression member 280 may include torque-limiting features such as those described in connection with the collet compression member 80 of fluid coupling 10 (e.g., an inner nut and an outer sleeve that cooperate to limit the torque that can be applied to the inner nut and, therefore, the force that can be applied to the collet).

The various components of the fluid coupling 210 may be manufactured of any suitable material or combination of materials (e.g., polymers, metals, ceramics, composites, etc.), although, as discussed herein, it may be preferred that the materials used for the strain relief, seal element, etc. be resiliently flexible.

The complete disclosure of the patents, patent documents, and publications cited in the Background, the Description of Illustrative Embodiments, and elsewhere herein are incorporated by reference in their entirety as if each were individually incorporated.

Illustrative embodiments of catheters and methods have been discussed and reference has been made to possible variations within the scope of this disclosure. These and other variations and modifications in the disclosure will be apparent to those skilled in the art without departing from the scope described herein, and it should be understood that this disclosure is not limited to the illustrative embodiments set forth herein.

What is claimed is:

1. A fluid coupling apparatus comprising:
   a housing comprising a proximal end, a distal end, and a longitudinal axis extending between the proximal end and the distal end of the housing, wherein the housing further comprises:
      a primary bore comprising an opening facing the distal end of the housing and a proximal face located within the bore, the proximal face facing the distal end of the housing, and
      a supply line passage formed in the housing, the supply line passage extending from the proximal end of the housing to an opening in the proximal face of the primary bore;
   a sleeve comprising a proximal end located in the primary bore, wherein the sleeve further comprises:
      a seal end facing the proximal face of the primary bore,
      a collet bore comprising a collet compression surface at a proximal end and an opening at a distal end, and
      a sleeve passage extending from the proximal end of the sleeve into the collet bore;
   a collet comprising a proximal end located in the collet bore of the sleeve, wherein the collet further comprises:
      a plurality of collet fingers surrounding a collet passage, wherein each of the collet fingers comprises an inclined surface proximate the proximal end of the collet,
      wherein the inclined surfaces of the plurality of collet fingers are in contact with the collet compression surface of the sleeve such that movement of the collet in a proximal direction towards the proximal end of the housing forces the collet fingers towards a center of the collet passage;
   a compliance member comprising a proximal end in contact with the distal end of the collet, and wherein the compliance member comprises a resiliently compressible elastomeric polymer; and
   a collet compression member engaged with the housing, wherein the collet compression member comprises an inner surface, an outer surface facing away from the inner surface, and a tubing passage formed through the collet compression member from the inner surface to the outer surface;
   wherein advancement of the collet compression member in the proximal direction towards the proximal end of the housing causes the following:
      the inner surface of the collet compression member is forced against a distal end of the compliance member such that the proximal end of the compliance member is forced against the collet,
      the inclined surfaces of the plurality of collet fingers are forced against the collet compression surface of the sleeve, and
      the seal end of the sleeve is forced towards the proximal face of the primary bore.

2. An apparatus according to claim 1, wherein a seal element is located between the proximal face of the primary bore and the seal end of the sleeve, and wherein advancement of the collet compression member in a proximal direction towards the proximal end of the housing compresses the seal element between the seal end of the sleeve and the proximal face of the primary bore.

3. An apparatus according to claim 2, wherein the seal element comprises an O-ring attached to the seal end of the sleeve.

4. An apparatus according to claim 2, wherein the material forming the seal end of the sleeve is softer than the material forming the proximal face of the primary bore.

5. An apparatus according to claim 4, wherein the seal end of the sleeve is formed of polymeric material and the proximal face of the primary bore is formed of metallic material.

6. An apparatus according to claim 1 further comprising a guide member located in the collet passage, wherein the guide member comprises a guide bore extending from a guide surface at a distal end of the guide member towards a proximal end of the guide member.

7. An apparatus according to claim 1, wherein the primary bore, the supply line passage, the collet bore, the collet passage, and the tubing passage are aligned along the longitudinal axis.

8. An apparatus according to claim 1, wherein the sleeve is constructed of a sleeve polymer, and wherein the resiliently compressible elastomeric polymer of the compliance member has a durometer that is less than a durometer of the sleeve polymer.

9. An apparatus according to claim 1, wherein a distance between the seal end of the sleeve and the proximal end of the collet is less than a length of the sleeve between the proximal end and the distal end of the sleeve, wherein the distance and the length are measured along the longitudinal axis.

10. An apparatus according to claim 1, wherein the proximal end of the collet is closer to the proximal end of the sleeve than to a distal end of the sleeve.

11. An apparatus according to claim 1, wherein the compliance member comprises a proximal tube and a distal tube, wherein the proximal tube is located proximally from the distal tube.

12. An apparatus according to claim 1, when the plurality of collet fingers are forced towards the center of the collet passage by the collet compression surface, the collet passage forms a generally circular bore between the collet fingers.

13. An apparatus according to claim 1, wherein the collet compression member and the housing are threadably engaged with each other such that rotation of one or both of the collet compression member and the housing moves the inner surface of the collet compression member towards the proximal end of the fluid coupling.

14. An apparatus according to claim 1, wherein the collet compression member comprises an inner nut and an outer sleeve fitted over the inner nut, wherein the inner surface of the collet compression member is located on the inner nut.

15. An apparatus according to claim 14, wherein the inner nut and the outer sleeve comprise a plurality of ridges facing each other, wherein rotation of the outer sleeve about the longitudinal axis forces the ridges to interact to rotate the inner nut.

16. An apparatus according to claim 15, wherein the ridges comprise a torque limiting structure such that the torque applied to the inner nut by the outer sleeve is limited when the ridges on the inner sleeve slip over the ridges on the inner nut when the outer sleeve is rotated in a first direction.

17. An apparatus according to claim 16, wherein rotation of the outer sleeve about the longitudinal axis in a second direction that is opposite from the first direction results in absolute engagement between the ridges on the outer sleeve and the ridges on the inner nut.

18. A fluid coupling apparatus comprising:
a housing comprising a proximal end, a distal end, and a longitudinal axis extending between the proximal end and the distal end of the housing, wherein the housing further comprises:
    a primary bore comprising an opening facing the distal end of the housing and a proximal face located within the primary bore, the proximal face facing the distal end of the housing, and
    a supply line passage formed in the housing, the supply line passage extending from the proximal end of the housing to an opening in the proximal face of the primary bore;
a sleeve comprising a proximal end located in the primary bore, wherein the sleeve further comprises:
    a seal cavity opening towards the proximal face of the primary bore,
    a collet bore comprising a collet compression surface at a distal end of the sleeve, wherein the collet bore opens towards the distal end of the sleeve, and
    a sleeve passage extending between the seal cavity and the collet bore;
a retention mechanism retaining the sleeve in the primary bore;
an amplifier piston located in the primary bore between the proximal face of the primary bore and the sleeve, wherein the amplifier piston comprises:
    a seal tip proximate a distal end of the amplifier piston, wherein the seal tip comprises a seal surface at the distal end of the amplifier piston, and wherein at least the seal surface of the seal tip is located in the seal cavity of the sleeve,
    a high pressure face at a proximal end of the amplifier piston, wherein the high pressure face faces the proximal surface of the primary bore, wherein the high pressure face comprises a larger surface area than the seal surface of the seal tip;
    a piston passage extending between the high pressure face and the seal surface of the amplifier piston,
    a piston seal located between the proximal end and the distal end of the amplifier piston, wherein fluid from the opening in the proximal face of the primary bore is restricted from flowing between an exterior surface of the amplifier piston and an interior surface of the primary bore to the distal end of the amplifier piston,
a seal element located in the seal cavity of the sleeve between the seal surface of the amplifier piston and a terminal surface of the seal cavity, wherein the seal element comprises a seal element passage extending through the seal element from a proximal end of the seal element to a distal end of the seal element, wherein the seal element comprises a resiliently compressible elastomeric polymer, and further wherein delivery of high pressure fluid through the fluid coupling apparatus forces the piston distally such that the seal element is compressed between the seal surface and the terminal surface of the seal cavity;
a collet comprising a proximal end located in the collet bore of the sleeve, wherein the collet further comprises:
    a plurality of collet fingers surrounding a collet passage, wherein each of the collet fingers comprises an inclined surface proximate the proximal end of the collet,
    wherein the inclined surfaces of the plurality of collet fingers are in contact with the collet compression surface of the sleeve such that movement of the collet in a proximal direction towards the proximal end of the housing forces the collet fingers towards a center of the collet passage; and
a collet compression member engaged with the sleeve, wherein the collet compression member comprises an inner surface, an outer surface facing away from the inner surface, and a tubing passage formed through the collet compression member from the inner surface to the outer surface, wherein advancement of the collet compression member in the proximal direction towards the proximal end of the housing forces the inclined surfaces of the plurality of collet fingers against the collet compression surface.

19. An apparatus according to claim 18, wherein a biasing element is located in the primary bore, the biasing element forcing the piston proximally away from the sleeve.

20. An apparatus according to claim 18, wherein the retention mechanism retaining the sleeve in the primary bore of the housing comprises a first snap-fit feature formed in an interior surface of the primary bore and a second snap fit feature formed in an outer surface of the sleeve, wherein the first snap fit feature and the second snap fit feature prevent removal of the sleeve from the primary bore in the absence of distortion of the sleeve and/or the housing.

* * * * *